(12) United States Patent
Goodearl

(10) Patent No.: US 6,277,565 B1
(45) Date of Patent: *Aug. 21, 2001

(54) OCT-3 GENE ENCODING TRANSPORTER-LIKE MOLECULES

(75) Inventor: Andrew David John Goodearl, Natick, MA (US)

(73) Assignee: Millennium Pharmaceuticals, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/964,127

(22) Filed: Nov. 6, 1997

(51) Int. Cl.[7] .............................. C12Q 1/68; C12P 19/34; C07H 21/04
(52) U.S. Cl. .......................... 435/6; 435/91.1; 435/91.2; 536/23.1; 536/23.5; 536/24.3; 536/24.31; 536/24.32
(58) Field of Search .............................. 435/6, 91.1, 91.2; 536/23.1, 23.5, 24.3, 24.31, 24.32

(56) References Cited

FOREIGN PATENT DOCUMENTS

WO93/16178 * 8/1993 (WO).
WO 98/48051 10/1998 (WO).

OTHER PUBLICATIONS

Lopez–Nieto et al., "Molecular Cloning and Characterization of NKT, a Gene Product Related to the Organic Cation . . . " J. of Biol. Chem. 272(10):6471–6478, 1997.

Okuda et al., "cDNA Cloning and Functional Expression of a Novel Rat Kidney Organic Cation Transporter, OCT2" Biochem. and Biophys. Res. Comm. 224:500–507, 1996.

Simonson et al., "Molecular cloning and characterization of a novel liver–specific transport protein" J. of Cell Science 107:1065–1072, 1994.

Grundemann et al., "Drug excretion mediated by a new prototype of polyspecific transporter" Nature 372:549, 1994.

* cited by examiner

*Primary Examiner*—Kenneth R. Horlick
*Assistant Examiner*—Jeffrey Siew
(74) *Attorney, Agent, or Firm*—Millennium Pharmaceuticals, Inc.

(57) ABSTRACT

The invention relates to OCT-3 polypeptides, nucleic acid molecules encoding OCT-3, and uses thereof. OCT-3 is a protein that is expressed in the plasma membrane of biological cells, across which it regulates the transport of organic molecules.

23 Claims, 5 Drawing Sheets

```
GTCGACCCACGCGTCCGCCCACGCGTCCGGGAGGCGCCCGCGGCTGCAGAGCTGCAGAGCGGGATCTCTTCGAGCTGTC    79
TGTGTCCGGGCAGCCGGCGCGCAACTGAGCCAGAGGACAGCGCATCCTTTCGGCGCGGGCCGGCAGGGCCCCTGCGGTC   158
GGCAAGCTGGCTCCCCGGGTGGCCACCGGGACCCCCGAGCCAATGGCGGGGGCGGCGGCAAAATCGACAACACTGTAG    237
AGATCACCCCCACCTCCAACGGACAGGTCGGGACCCTCGGAGATGCGGTGCCCACGGAGCAGCTGCAGGGTGAGCGGGA   316
GCGCGAGCGGGAGGGGGAGGGAGACGCGGGCGGCGACGGACTGGGCAGCAGCCTGTCGCTGGCCGTGCCCCCAGGCCCC   395
CTCAGCTTTGAGGCGCTGCTCGCCCAGGTGGGGGCGCTGGGCGGCGGCCAGCAGCTGCAGCTCGGCCTCTGCTGCCTGC   474
                              M   A   S   D   P   I   F   T   L   A   P   P   L   H    14
CGGTGCTCTTCGTGGCTCTGGGC ATG GCC TCG GAC CCC ATC TTC ACG CTG GCG CCC CCG CTG CAT    539

C   H   Y   G   A   F   P   P   N   A   S   G   W   E   Q   P   P   N   A   S     34
TGC CAC TAC GGG GCC TTC CCC CCT AAT GCC TCT GGC TGG GAG CAG CCT CCC AAT GCC AGC    599

G   V   S   V   A   S   A   A   L   A   A   S   A   A   S   R   V   A   T   S     54
GGC GTC AGC GTC GCC AGC GCT GCC CTA GCA GCC AGC GCC GCC AGC CGT GTC GCC ACC AGT    659

T   D   P   S   C   S   G   F   A   P   P   D   F   N   H   C   L   K   D   W     74
ACC GAC CCC TCG TGC AGC GGC TTC GCC CCG CCG GAC TTC AAC CAT TGC CTC AAG GAT TGG    719

D   Y   N   G   L   P   V   L   T   T   N   A   I   G   Q   W   D   L   V   C     94
GAC TAT AAT GGC CTT CCT GTG CTC ACC ACC AAC GCC ATC GGC CAG TGG GAT CTG GTG TGT    779

D   L   G   W   Q   V   I   L   E   Q   I   L   F   I   L   G   F   A   S   G    114
GAC CTG GGC TGG CAG GTG ATC CTG GAG CAG ATC CTC TTC ATC TTG GGC TTT GCC TCC GGC    839

Y   L   F   L   G   Y   P   A   D   R   F   G   R   G   I   V   L   L   T        134
TAC CTG TTC CTG GGT TAC CCC GCA GAC AGA TTT GGC CGT CGC GGG ATT GTG CTG CTG ACC    899

L   G   L   V   G   P   C   G   V   G   G   A   A   A   G   S   S   T   G   V    154
TTG GGG CTG GTG GGC CCC TGT GGA GTA GGA GGG GCT GCT GCA GGC TCC TCC ACA GGC GTC    959

M   A   L   R   F   L   L   G   F   L   L   A   G   V   D   L   G   V   Y   L    174
ATG GCC CTC CGA TTC CTC TTG GGC TTT CTG CTT GCC GGT GTT GAC CTG GGT GTC TAC CTG   1019

M   R   L   E   L   C   D   P   T   Q   R   L   R   V   A   L   A   G   E   L    194
ATG CGC CTG GAG CTG TGC GAC CCA ACC CAG AGG CTT CGG GTG GCC CTG GCA GGG GAG TTG   1079

V   G   V   G   G   H   F   L   F   L   G   L   A   L   V   S   K   D   W   R    214
GTG GGG GTG GGA GGG CAC TTC CTG TTC CTG GGC CTG GCC CTT GTC TCT AAG GAT TGG CGA   1139

F   L   Q   R   M   I   T   A   P   C   I   L   F   L   F   Y   G   W   P   G    234
TTC CTA CAG CGA ATG ATC ACC GCT CCC TGC ATC CTC TTC CTG TTT TAT GGC TGG CCT GGT   1199

L   F   L   E   S   A   R   W   L   I   V   K   R   Q   I   E   E   A   Q   S    254
TTG TTC CTG GAG TCC GCA CGG TGG CTG ATA GTG AAG CGG CAG ATT GAG GAG GCT CAG TCT   1259

V   L   R   I   L   A   E   R   N   R   P   H   G   Q   M   L   G   E   E   A    274
GTG CTG AGG ATC CTG GCT GAG CGA AAC CGG CCC CAT GGG CAG ATG CTG GGG GAG GAG GCC   1319

Q   E   A   L   Q   D   L   E   N   T   C   P   L   P   A   T   S   S   F   S    294
CAG GAG GCC CTG CAG GAC CTG GAG AAT ACC TGC CCT CTC CCT GCA ACA TCC TCC TTT TCC   1379

F   A   S   L   L   N   Y   R   N   I   W   K   N   L   L   I   L   G   F   T    314
TTT GCT TCC CTC CTC AAC TAC CGC AAC ATC TGG AAA AAT CTG CTT ATC CTG GGC TTC ACC   1439

N   F   I   A   H   A   I   R   H   C   Y   Q   P   V   G   G   G   G   S   P    334
AAC TTC ATT GCC CAT GCC ATT CGC CAC TGC TAC CAG CCT GTG GGA GGA GGA GGG AGC CCA   1499

S   D   F   Y   L   C   S   L   L   A   S   G   T   A   A   L   A   C   V   F    354
TCG GAC TTC TAC CTG TGC TCT CTG CTG GCC AGC GGC ACC GCA GCC CTG GCC TGT GTC TTC   1559

L   G   V   T   V   D   R   F   G   R   R   G   I   L   L   L   S   M   T   L    374
CTG GGG GTC ACC GTG GAC CGA TTT GGC CGC CGG GGC ATC CTT CTT CTC TCC ATG ACC CTT   1619

T   G   I   A   S   L   V   L   L   G   L   W   D   Y   L   N   E   A   A   I    394
ACC GGC ATT GCT TCC CTG GTC CTG CTG GGC CTG TGG GAT TAT CTG AAC GAG GCT GCC ATC   1679

T   T   F   S   V   L   G   L   F   S   S   Q   A   A   A   I   L   S   T   L    414
ACC ACT TTC TCT GTC CTT GGG CTC TTC TCC TCC CAA GCT GCC GCC ATC CTC AGC ACC CTC   1739

L   A   A   E   V   I   P   T   T   V   R   G   R   G   L   G   L   I   M   A    434
CTT GCT GCT GAG GTC ATC CCC ACC ACT GTC CGG GGC CGT GGC CTG GGC CTG ATC ATG GCT   1799

L   G   A   L   G   G   L   S   G   P   A   Q   R   L   H   M   G   H   G   A    454
CTA GGG GCG CTT GGA GGA CTG AGC GGC CCG GCC CAG CGC CTC CAC ATG GGC CAT GGA GCC   1859
```

```
 F   L   Q   H   V   V   L   A   A   C   A   L   L   C   I   L   S   I   M   L    474
TTC CTG CAG CAC GTG GTG CTG GCG GCC TGC GCC CTC CTC TGC ATT CTC AGC ATT ATG CTG   1919

L   P   E   T   K   R   K   L   L   P   E   V   L   R   D   G   E   L   C   R    494
CTG CCG GAG ACC AAG CGC AAG CTC CTG CCC GAG GTG CTC CGG GAC GGG GAG CTG TGT CGC   1979

R   P   S   L   L   R   Q   P   P   P   T   R   C   D   H   V   P   L   L   A    514
CGG CCT TCC CTG CTG CGG CAG CCA CCC CCT ACC CGC TGT GAC CAC GTC CCG CTG CTT GCC   2039

T   P   N   P   A   L   *  (SEQ ID NO:2)                                          521
ACC CCC AAC CCT GCC CTC TGA                                                       2060
GCGGCCTCTGAGTACCCTGGCGGGAGGCTGGCCCACACAGAAAGGTGGCAAGAAGATCGGGAAGACTGAGTAGGGAAGG   2139
CAGGGCTGCCCAGAAGTCTCAGAGGCACCTCACGCCAGCCATCGCGGAGAGCTCAGAGGGCCGTCCCCACCCTGCCTCC   2218
TCCCTGCTGCTTTGCATTCACTTCCTTGGCCAGAGTCAGGGGACAGGGAGAGAGCTCCACACTGTAACCACTGGGTCTG   2297
GGCTCCATCCTGCGCCCAAAGACATCCACCCAGACCTCATTATTTCTTGCTCTATCATTCTGTTTCAATAAAGACATTT   2376
GGAATAAACGAGCAAAAAAAAAAAAAAAAAAAAAAAAAAAAGGGCGGCCGCTCTAGAGGATCCAAGCTTACGTACGCGTGC 2455
ATGCG (SEQ ID NO:1)                                                               2460
```

```
GTCGACCCACGCGTCCGGACCAAGGAGGCGCCCGCGGCTGCAGAGCTGCAGAGCGGGATCTCTTCGAGCTGTCTGTGTC   79
CGGGCAGCCGGCGCGCAACTGAGCCAGAGGACAGCGCATCCTTTCGGCGCGGGCCGGCAGGGCCCCTGCGGTCGGCAAG  158
CTGGCTCCCCGGGTGGCCACCGGGACCCCCGAGCCCAATGGCGGGGCGGCGGCAAAATCGACAACACTGTAGAGATCA   237
CCCCCACCTCCAACGGACAGGTCGGGACCCTCGGAGATGCGGTGCCCACGGAGCAGCTGCAGGGTGAGCGGGAGCGCGA  316
GCGGGAGGGGGAGGGAGACGCGGGCGGCGACGGACTGGGCAGCAGCCTGTCGCTGGCCGTGCCCCCAGGCCCCTCAGC   395
TTTGAGGCGCTGCTCGCCCAGGTGGGGGCGCTGGGCGGCGGCCAGCAGCTGCAGCTCGGCCTCTGCTGCCTGCCGGTGC  474
```

|                       |                                                                 |     |
|-----------------------|-----------------------------------------------------------------|-----|
|                       M   A   S   D   P   I   F   T   L   A   P   P   L   H   C   | 15  |
| TCTTCGTGGCTCTGGGC     ATG GCC TCG GAC CCC ATC TTC ACG CTG GCG CCC CCG CTG CAT TGC | 536 |

```
          H   Y   G   A   F   P   P   N   A   S   G   W   E   Q   P   P   N   A   S   G    35
          CAC TAC GGG GCC TTC CCC CCT AAT GCC TCT GGC TGG GAG CAG CCT CCC AAT GCC AGC GGC  596

V   S   V   A   S   A   A   L   A   A   S   A   A   S   R   V   A   T   S   T    55
          GTC AGC GTC GCC AGC GCT GCC CTA GCA GCC AGC GCC GCC AGC CGT GTC GCC ACC AGT ACC  656

D   P   S   C   S   G   F   A   P   P   D   F   N   H   C   L   K   D   W   D    75
          GAC CCC TCG TGC AGC GGC TTC GCC CCG CCG GAC TTC AAC CAT TGC CTC AAG GAT TGG GAC  716

Y   N   G   L   P   V   L   T   T   N   A   I   G   Q   W   D   L   V   C   D    95
          TAT AAT GGC CTT CCT GTG CTC ACC ACC AAC GCC ATC GGC CAG TGG GAT CTG GTG TGT GAC  776

L   G   W   Q   V   I   L   E   Q   I   L   F   I   L   G   F   A   S   G   Y   115
          CTG GGC TGG CAG GTG ATC CTG GAG CAG ATC CTC TTC ATC TTG GGC TTT GCC TCC GGC TAC  836

L   F   L   G   Y   P   A   D   R   F   G   R   R   G   I   V   L   L   T   L   135
          CTG TTC CTG GGT TAC CCC GCA GAC AGA TTT GGC CGT CGC GGG ATT GTG CTG CTG ACC TTG  896

G   L   V   G   P   C   G   V   G   G   A   A   G   S   S   T   G   V   M       155
          GGG CTG GTG GGC CCC TGT GGA GTA GGA GGG GCT GCT GCA GGC TCC TCC ACA GGC GTC ATG  956

A   L   R   F   L   L   G   F   L   L   A   G   V   D   L   G   V   Y   L   M   175
          GCC CTC CGA TTC CTC TTG GGC TTT CTG CTT GCC GGT GTT GAC CTG GGT GTC TAC CTG ATG 1016

R   L   E   L   C   D   P   T   Q   R   L   R   V   A   L   A   G   E   L   V   195
          CGC CTG GAG CTG TGC GAC CCA ACC CAG AGG CTT CGG GTG GCC CTG GCA GGG GAG TTG GTG 1076

G   V   G   G   H   F   L   F   L   G   L   A   L   V   S   K   D   W   R   F   215
          GGG GTG GGA GGG CAC TTC CTG TTC CTG GGC CTG GCC CTT GTC TCT AAG GAT TGG CGA TTC 1136

L   Q   R   M   I   T   A   P   C   I   L   F   L   F   Y   G   W   P   G   L   235
          CTA CAG CGA ATG ATC ACC GCT CCC TGC ATC CTC TTC CTG TTT TAT GGC TGG CCT GGT TTG 1196

F   L   E   S   A   R   W   L   I   V   K   R   Q   I   E   E   A   Q   S   V   255
          TTC CTG GAG TCC GCA CGG TGG CTG ATA GTG AAG CGG CAG ATT GAG GAG GCT CAG TCT GTG 1256

L   R   I   L   A   E   R   N   R   P   H   G   Q   M   L   G   E   E   A   Q   275
          CTG AGG ATC CTG GCT GAG CGA AAC CGG CCC CAT GGG CAG ATG CTG GGG GAG GAG GCC CAG 1316

E   A   L   Q   D   L   E   S   S   T   L   *    (SEQ ID NO:4)                  287
          GAG GCC CTG CAG GAC CTG GAG AGC TCC ACA CTG TAA                                  1352
          CCACTGGGTCTGGGCTCCATCCTGCGCCCAAAGACATCCACCCAGACCTCATTATTTCTTGCTCTATCATTCTGTTTCA 1431
          ATAAAGACATTTGGAATAAACGAGCATAAAAAAAAAAAAAAAAAAAAAAAAAAAAAAAAAA (SEQ ID NO:3)       1490
```

FIG. 2

```
  V   D   P   R   V   R   G   L   A   L   V   S   K   D   W   R   F   L   Q   R    20
GTC GAC CCA CGC GTC CGG GGC CTG GCC CTT GTC TCT AAG GAC TGG CGG TTC CTG CAG CGA    60

M   I   T   A   P   C   I   L   F   L   F   Y   G   W   P   G   L   F   L   E    40
ATG ATC ACC GCT CCT TGC ATC CTC TTC CTG TTT TAT GGC TGG CCC GGT CTG TTT CTG GAG   120

S   A   R   W   L   I   V   K   R   Q   I   E   E   A   Q   S   V   L   R   I    60
TCC GCA CGG TGG CTG ATA GTG AAA CGG CAG ATT GAG GAA GCC CAG TCT GTG CTG AGG ATC   180

L   A   E   R   N   R   P   H   G   Q   M   L   G   E   E   A   Q   E   A   L    80
CTG GCT GAG CGA AAC CGG CCC CAT GGC CAG ATG CTG GGA GAA GAG GCC CAG GAA GCC CTG   240

Q   E   L   E   N   T   C   P   L   P   T   T   S   T   F   S   F   A   S   L   100
CAG GAG CTG GAG AAT ACC TGT CCT CTC CCC ACA ACG TCC ACC TTT TCC TTC GCC TCC CTC   300

L   N   Y   R   N   I   W   K   N   L   L   I   L   G   F   T   N   F   I   A   120
CTC AAC TAC CGA AAC ATC TGG AAA AAT CTG CTT ATC CTG GGC TTC ACC AAC TTT ATC GCC   360

H   A   I   R   H   C   Y   Q   P   V   G   G   G   G   S   P   S   D   F   Y   140
CAT GCC ATT CGC CAC TGC TAC CAG CCT GTG GGA GGA GGA GGG AGC CCA TCA GAC TTC TAC   420

L   C   S   L   L   A   S   G   T   A   A   L   A   C   V   F   L   G   V   T   160
TTG TGC TCT CTT CTG GCC AGC GGC ACA GCA GCC CTG GCC TGC GTC TTC CTG GGG GTG ACC   480

V   D   R   F   G   R   R   G   I   L   L   S   M   T   L   T   G   I   A   180
GTG GAC CGT TTC GGC CGT CGG GGC ATC CTG CTT CTC TCA ATG ACT CTC ACG GGG ATT GCA   540

S   L   V   L   L   G   L   W   D   Y   L   N   D   A   A   I   T   T   F   S   200
TCC CTG GTC TTG CTG GGC CTG TGG GAT TAT CTG AAC GAT GCT GCC ATC ACA ACC TTC TCG   600

V   L   G   L   F   S   S   Q   A   S   A   I   L   S   T   L   L   A   A   E   220
GTC CTC GGA CTC TTC TCC TCC CAA GCT TCT GCT ATC CTC AGT ACC CTC CTT GCT GCT GAA   660

V   I   P   T   T   V   R   G   R   G   L   G   L   I   M   A   L   G   A   L   240
GTC ATC CCC ACC ACT GTC CGG GGC CGT GGC CTG GGC CTT ATC ATG GCA CTT GGG GCG CTT   720

G   G   L   S   C   P   A   Q   R   L   H   M   G   H   G   A   F   L   Q   H   260
GGA GGG CTG AGC TGT CCA GCT CAG CGC CTC CAC ATG GGC CAT GGA GCT TTC CTG CAG CAT   780

V   V   L   A   A   C   A   L   L   C   I   L   S   I   M   L   L   P   E   T   280
GTG GTA CTG GCG GCC TGT GCC CTC CTC TGC ATC CTT AGC ATC ATG CTG CTG CCA GAG ACC   840

K   R   K   L   L   P   E   V   L   R   D   G   E   L   C   R   R   P   S   L   300
AAG CGC AAG CTT CTG CCA GAG GTA CTC CGG GAT GGG GAA CTG TGC CGT CGG CCT TCC CTG   900

L   R   Q   P   P   P   N   R   C   D   H   V   P   L   L   A   T   P   N   P   320
CTG AGG CAG CCA CCT CCT AAC CGC TGT GAC CAT GTC CCC CTG CTA GCC ACT CCT AAT CCT   960

A   L   *   (SEQ ID NO:6)                                                         323
GCC CTC TAA                                                                         969

GCAGCCTCTGAGCCTGGTGGGAGGCTGGCCATTTAGAAAGGTGACGGAGGGCTGGCTAGCAAGATAGACGGAGAGGCAA   1048

GGCCACCCTGTACATACAAAAGGCTCCAAGGCGCCTCACGCCATCTAGGAGAGCTCAGAGTGCCATTCCCAACCCCCTC   1127

TCCTCCCCGCTGCTTTCTGTTCACTTCATCAGCAAGAGTCAGGACGGGGATAGCATCTCGCTATAACCGTTAGGTCTGG   1206

GATCCATCCTATGCCCAAAGACATTTTCCCAGACCTTGCTCTTTCTCGCTCTTCATTCTGTTTCAATAAAAGACATTTT   1285

GAATAAATGAGCATTTCATAGCCTGGGAAAAAAAAAAAAAAAAAAAAAAAAAAAAAAAAAAAAAAAAAAAAAAAAAAAA   1364

AAAAAAAAAAAAAAAAAAAAAAAAAAAAAAAAAAAAAAAGGGCGGCCGC    (SEQ ID NO:5)                1411
```

FIG. 3

Fig. 4A  OCT Consensus: GYXXDRXGRR (with K above position 7)
        OCT-3:         GYPADRFGRR (119-128)

Fig. 4B  OCT Consensus: RXLXGXXLAXXXXXXXXXLXTEWXXXXXR (with I, SK, M F above)
        OCT-3:         RFLLGFLLAGVDLGVYLMRLELCDPTQR (158-185)

Fig. 4C  OCT Consensus: PESXRWL (with I, Y above)
        OCT-3:         LESARWL (237-243)

Fig. 4D  OCT Consensus: LLPETK (with L above)
        OCT-3:         LLPETK (474-479)

Fig. 4E  OCT Consensus: LXNXELYPTXXRNLG (with T, QTR above)
        OCT-3:         LLAAEVIPTTVRGRG (415-428)

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 2460 base pairs
       (B) TYPE: nucleic acid
       (C) STRANDEDNESS: single
       (D) TOPOLOGY: linear (ii) MOLECULE TYPE: Genomic DNA (ix) FEATURE:
       (A) NAME/KEY: Coding Sequence
       (B) LOCATION: 498...2057

(xi) SEQUENCE DESCRIPTION: SEQ ID NO:1:

```
GTCGACCCAC GCGTCCGCCC ACGCGTCCGG GAGGCGCCCG CGGCTGCAGA GCTGCAGAGC      60
GGGATCTCTT CGAGCTGTCT GTGTCCGGGC AGCCGGCGCG CAACTGAGCC AGAGGACAGC     120

GCATCCTTTC GGCGCGGGCC GGCAGGGCCC CTGCGGTCGG CAAGCTGGCT CCCCGGGTGG     180

CCACCGGGAC CCCCGAGCCC AATGGCGGGG GCGGCGGCAA AATCGACAAC ACTGTAGAGA     240

TCACCCCCAC CTCCAACGGA CAGGTCGGGA CCCTCGGAGA TGCGGTGCCC ACGGAGCAGC     300

TGCAGGGTGA GCGGGAGCGC GAGCGGGAGG GGGAGGGAGA CGCGGGCGGC GACGGACTGG     360

GCAGCAGCCT GTCGCTGGCC GTGCCCCCAG GCCCCCTCAG CTTTGAGGCG CTGCTCGCCC     420

AGGTGGGGGC GCTGGGCGGC GGCCAGCAGC TGCAGCTCGG CCTCTGCTGC CTGCCGGTGC     480

TCTTCGTGGC TCTGGGC ATG GCC TCG GAC CCC ATC TTC ACG CTG GCG CCC       530
                    Met Ala Ser Asp Pro Ile Phe Thr Leu Ala Pro
                     1               5                  10

CCG CTG CAT TGC CAC TAC GGG GCC TTC CCC CCT AAT GCC TCT GGC TGG       578
Pro Leu His Cys His Tyr Gly Ala Phe Pro Pro Asn Ala Ser Gly Trp
             15                  20                  25

GAG CAG CCT CCC AAT GCC AGC GGC GTC AGC GTC GCC AGC GCT GCC CTA       626
Glu Gln Pro Pro Asn Ala Ser Gly Val Ser Val Ala Ser Ala Ala Leu
         30                  35                  40

GCA GCC AGC GCC GCC AGC CGT GTC GCC ACC AGT ACC GAC CCC TCG TGC       674
Ala Ala Ser Ala Ala Ser Arg Val Ala Thr Ser Thr Asp Pro Ser Cys
     45                  50                  55

AGC GGC TTC GCC CCG CCG GAC TTC AAC CAT TGC CTC AAG GAT TGG GAC       722
Ser Gly Phe Ala Pro Pro Asp Phe Asn His Cys Leu Lys Asp Trp Asp
 60                  65                  70                  75

TAT AAT GGC CTT CCT GTG CTC ACC ACC AAC GCC ATC GGC CAG TGG GAT       770
Tyr Asn Gly Leu Pro Val Leu Thr Thr Asn Ala Ile Gly Gln Trp Asp
                 80                  85                  90

CTG GTG TGT GAC CTG GGC TGG CAG GTG ATC CTG GAG CAG ATC CTC TTC       818
Leu Val Cys Asp Leu Gly Trp Gln Val Ile Leu Glu Gln Ile Leu Phe
             95                 100                 105

ATC TTG GGC TTT GCC TCC GGC TAC CTG TTC CTG GGT TAC CCC GCA GAC       866
Ile Leu Gly Phe Ala Ser Gly Tyr Leu Phe Leu Gly Tyr Pro Ala Asp
         110                 115                 120

AGA TTT GGC CGT CGC GGG ATT GTG CTG CTG ACC TTG GGG CTG GTG GGC       914
Arg Phe Gly Arg Arg Gly Ile Val Leu Leu Thr Leu Gly Leu Val Gly
     125                 130                 135

CCC TGT GGA GTA GGA GGG GCT GCT GCA GGC TCC TCC ACA GGC GTC ATG       962
Pro Cys Gly Val Gly Gly Ala Ala Ala Gly Ser Ser Thr Gly Val Met
140                 145                 150                 155

GCC CTC CGA TTC CTC TTG GGC TTT CTG CTT GCC GGT GTT GAC CTG GGT      1010
```

```
                                                                    -continued Ala Leu Arg Phe Leu Leu Gly Phe Leu Leu Ala Gly Val Asp Leu Gly
                160                 165             170

GTC TAC CTG ATG CGC CTG GAG CTG TGC GAC CCA ACC CAG AGG CTT CGG     1058
Val Tyr Leu Met Arg Leu Glu Leu Cys Asp Pro Thr Gln Arg Leu Arg
            175                 180              185

GTG GCC CTG GCA GGG GAG TTG GTG GGG GTG GGA GGG CAC TTC CTG TTC     1106
Val Ala Leu Ala Gly Glu Leu Val Gly Val Gly Gly His Phe Leu Phe
        190                 195             200

CTG GGC CTG GCC CTT GTC TCT AAG GAT TGG CGA TTC CTA CAG CGA ATG     1154
Leu Gly Leu Ala Leu Val Ser Lys Asp Trp Arg Phe Leu Gln Arg Met
    205                 210              215

ATC ACC GCT CCC TGC ATC CTC TTC CTG TTT TAT GGC TGG CCT GGT TTG     1202
Ile Thr Ala Pro Cys Ile Leu Phe Leu Phe Tyr Gly Trp Pro Gly Leu
220                 225             230                 235

TTC CTG GAG TCC GCA CGG TGG CTG ATA GTG AAG CGG CAG ATT GAG GAG     1250
Phe Leu Glu Ser Ala Arg Trp Leu Ile Val Lys Arg Gln Ile Glu Glu
                240             245             250

GCT CAG TCT GTG CTG AGG ATC CTG GCT GAG CGA AAC CGG CCC CAT GGG     1298
Ala Gln Ser Val Leu Arg Ile Leu Ala Glu Arg Asn Arg Pro His Gly
            255             260             265

CAG ATG CTG GGG GAG GAG GCC CAG GAG GCC CTG CAG GAC CTG GAG AAT     1346
Gln Met Leu Gly Glu Glu Ala Gln Glu Ala Leu Gln Asp Leu Glu Asn
        270             275             280

ACC TGC CCT CTC CCT GCA ACA TCC TCC TTT TCC TTT GCT TCC CTC CTC     1394
Thr Cys Pro Leu Pro Ala Thr Ser Ser Phe Ser Phe Ala Ser Leu Leu
    285             290             295

AAC TAC CGC AAC ATC TGG AAA AAT CTG CTT ATC CTG GGC TTC ACC AAC     1442
Asn Tyr Arg Asn Ile Trp Lys Asn Leu Leu Ile Leu Gly Phe Thr Asn
300             305             310             315

TTC ATT GCC CAT GCC ATT CGC CAC TGC TAC CAG CCT GTG GGA GGA GGA     1490
Phe Ile Ala His Ala Ile Arg His Cys Tyr Gln Pro Val Gly Gly Gly
            320             325             330

GGG AGC CCA TCG GAC TTC TAC CTG TGC TCT CTG CTG GCC AGC GGC ACC     1538
Gly Ser Pro Ser Asp Phe Tyr Leu Cys Ser Leu Leu Ala Ser Gly Thr
        335             340             345

GCA GCC CTG GCC TGT GTC TTC CTG GGG GTC ACC GTG GAC CGA TTT GGC     1586
Ala Ala Leu Ala Cys Val Phe Leu Gly Val Thr Val Asp Arg Phe Gly
    350             355             360

CGC CGG GGC ATC CTT CTT CTC TCC ATG ACC CTT ACC GGC ATT GCT TCC     1634
Arg Arg Gly Ile Leu Leu Leu Ser Met Thr Leu Thr Gly Ile Ala Ser
365             370             375

CTG GTC CTG CTG GGC CTG TGG GAT TAT CTG AAC GAG GCT GCC ATC ACC     1682
Leu Val Leu Leu Gly Leu Trp Asp Tyr Leu Asn Glu Ala Ala Ile Thr
380             385             390             395

ACT TTC TCT GTC CTT GGG CTC TTC TCC TCC CAA GCT GCC GCC ATC CTC     1730
Thr Phe Ser Val Leu Gly Leu Phe Ser Ser Gln Ala Ala Ala Ile Leu
            400             405             410

AGC ACC CTC CTT GCT GCT GAG GTC ATC CCC ACC ACT GTC CGG GGC CGT     1778
Ser Thr Leu Leu Ala Ala Glu Val Ile Pro Thr Thr Val Arg Gly Arg
        415             420             425

GGC CTG GGC CTG ATC ATG GCT CTA GGG GCG CTT GGA GGA CTG AGC GGC     1826
Gly Leu Gly Leu Ile Met Ala Leu Gly Ala Leu Gly Gly Leu Ser Gly
    430             435             440

CCG GCC CAG CGC CTC CAC ATG GGC CAT GGA GCC TTC CTG CAG CAC GTG     1874
Pro Ala Gln Arg Leu His Met Gly His Gly Ala Phe Leu Gln His Val
445             450             455

GTG CTG GCG GCC TGC GCC CTC CTC TGC ATT CTC AGC ATT ATG CTG CTG     1922
Val Leu Ala Ala Cys Ala Leu Leu Cys Ile Leu Ser Ile Met Leu Leu
460             465             470             475
```

```
CCG GAG ACC AAG CGC AAG CTC CTG CCC GAG GTG CTC CGG GAC GGG GAG     1970
Pro Glu Thr Lys Arg Lys Leu Leu Pro Glu Val Leu Arg Asp Gly Glu
                480                 485                 490

CTG TGT CGC CGG CCT TCC CTG CTG CGG CAG CCA CCC CCT ACC CGC TGT     2018
Leu Cys Arg Arg Pro Ser Leu Leu Arg Gln Pro Pro Pro Thr Arg Cys
            495                 500                 505

GAC CAC GTC CCG CTG CTT GCC ACC CCC AAC CCT GCC CTC TGAGCGGCCT      2067
Asp His Val Pro Leu Leu Ala Thr Pro Asn Pro Ala Leu
        510                 515                 520

CTGAGTACCC TGGCGGGAGG CTGGCCCACA CAGAAAGGTG GCAAGAAGAT CGGGAAGACT   2127

GAGTAGGGAA GGCAGGGCTG CCCAGAAGTC TCAGAGGCAC CTCACGCCAG CCATCGCGGA   2187

GAGCTCAGAG GGCCGTCCCC ACCCTGCCTC CTCCCTGCTG CTTTGCATTC ACTTCCTTGG   2247

CCAGAGTCAG GGGACAGGGA GAGAGCTCCA CACTGTAACC ACTGGGTCTG GGCTCCATCC   2307

TGCGCCCAAA GACATCCACC CAGACCTCAT TATTTCTTGC TCTATCATTC TGTTTCAATA   2367

AAGACATTTG GAATAAACGA GCAAAAAAAA AAAAAAAAA AAAAAAAGG GCGGCCGCTC    2427

TAGAGGATCC AAGCTTACGT ACGCGTGCAT GCG                                2460

(2) INFORMATION FOR SEQ ID NO:2:

(i) SEQUENCE CHARACTERISTICS:
        (A) LENGTH: 520 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

Met Ala Ser Asp Pro Ile Phe Thr Leu Ala Pro Pro Leu His Cys His
 1               5                  10                  15

Tyr Gly Ala Phe Pro Pro Asn Ala Ser Gly Trp Glu Gln Pro Pro Asn
                20                  25                  30

Ala Ser Gly Val Ser Val Ala Ser Ala Leu Ala Ala Ser Ala Ala
            35                  40                  45

Ser Arg Val Ala Thr Ser Thr Asp Pro Ser Cys Ser Gly Phe Ala Pro
 50                  55                  60

Pro Asp Phe Asn His Cys Leu Lys Asp Trp Asp Tyr Asn Gly Leu Pro
 65                  70                  75                  80

Val Leu Thr Thr Asn Ala Ile Gly Gln Trp Asp Leu Val Cys Asp Leu
                85                  90                  95

Gly Trp Gln Val Ile Leu Glu Gln Ile Leu Phe Ile Leu Gly Phe Ala
            100                 105                 110

Ser Gly Tyr Leu Phe Leu Gly Tyr Pro Ala Asp Arg Phe Gly Arg Arg
        115                 120                 125

Gly Ile Val Leu Leu Thr Leu Gly Leu Val Gly Pro Cys Gly Val Gly
130                 135                 140

Gly Ala Ala Ala Gly Ser Ser Thr Gly Val Met Ala Leu Arg Phe Leu
145                 150                 155                 160

Leu Gly Phe Leu Leu Ala Gly Val Asp Leu Gly Val Tyr Leu Met Arg
                165                 170                 175

Leu Glu Leu Cys Asp Pro Thr Gln Arg Leu Arg Val Ala Leu Ala Gly
            180                 185                 190

Glu Leu Val Gly Val Gly Gly His Phe Leu Phe Leu Gly Leu Ala Leu
        195                 200                 205
```

```
Val Ser Lys Asp Trp Arg Phe Leu Gln Arg Met Ile Thr Ala Pro Cys
    210                 215                 220

Ile Leu Phe Leu Phe Tyr Gly Trp Pro Gly Leu Phe Leu Glu Ser Ala
225                 230                 235                 240

Arg Trp Leu Ile Val Lys Arg Gln Ile Glu Glu Ala Gln Ser Val Leu
                245                 250                 255

Arg Ile Leu Ala Glu Arg Asn Arg Pro His Gly Gln Met Leu Gly Glu
            260                 265                 270

Glu Ala Gln Glu Ala Leu Gln Asp Leu Glu Asn Thr Cys Pro Leu Pro
        275                 280                 285

Ala Thr Ser Ser Phe Ser Phe Ala Ser Leu Leu Asn Tyr Arg Asn Ile
    290                 295                 300

Trp Lys Asn Leu Leu Ile Leu Gly Phe Thr Asn Phe Ile Ala His Ala
305                 310                 315                 320

Ile Arg His Cys Tyr Gln Pro Val Gly Gly Gly Ser Pro Ser Asp
                325                 330                 335

Phe Tyr Leu Cys Ser Leu Leu Ala Ser Gly Thr Ala Leu Ala Cys
            340                 345                 350

Val Phe Leu Gly Val Thr Val Asp Arg Phe Gly Arg Gly Ile Leu
        355                 360                 365

Leu Leu Ser Met Thr Leu Thr Gly Ile Ala Ser Leu Val Leu Leu Gly
    370                 375                 380

Leu Trp Asp Tyr Leu Asn Glu Ala Ala Ile Thr Thr Phe Ser Val Leu
385                 390                 395                 400

Gly Leu Phe Ser Ser Gln Ala Ala Ile Leu Ser Thr Leu Leu Ala
            405                 410                 415

Ala Glu Val Ile Pro Thr Thr Val Arg Gly Arg Gly Leu Gly Leu Ile
            420                 425                 430

Met Ala Leu Gly Ala Leu Gly Gly Leu Ser Gly Pro Ala Gln Arg Leu
        435                 440                 445

His Met Gly His Gly Ala Phe Leu Gln His Val Val Leu Ala Ala Cys
    450                 455                 460

Ala Leu Leu Cys Ile Leu Ser Ile Met Leu Leu Pro Glu Thr Lys Arg
465                 470                 475                 480

Lys Leu Leu Pro Glu Val Leu Arg Asp Gly Glu Leu Cys Arg Arg Pro
                485                 490                 495

Ser Leu Leu Arg Gln Pro Pro Thr Arg Cys Asp His Val Pro Leu
            500                 505                 510

Leu Ala Thr Pro Asn Pro Ala Leu
        515                 520

(2) INFORMATION FOR SEQ ID NO:3:

(i) SEQUENCE CHARACTERISTICS:
        (A) LENGTH: 1490 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 492...1349

(xi) SEQUENCE DESCRIPTION: SEQ ID NO:3:

GTCGACCCAC GCGTCCGGAC CAAGGAGGCG CCCGCGGCTG CAGAGCTGCA GAGCGGGATC      60
```

```
TCTTCGAGCT GTCTGTGTCC GGGCAGCCGG CGCGCAACTG AGCCAGAGGA CAGCGCATCC      120

TTTCGGCGCG GGCCGGCAGG GCCCCTGCGG TCGGCAAGCT GGCTCCCCGG GTGGCCACCG      180

GGACCCCCGA GCCCAATGGC GGGGGCGGCG GCAAAATCGA CAACACTGTA GAGATCACCC      240

CCACCTCCAA CGGACAGGTC GGGACCCTCG GAGATGCGGT GCCCACGGAG CAGCTGCAGG      300

GTGAGCGGGA GCGCGAGCGG GAGGGGGAGG GAGACGCGGG CGGCGACGGA CTGGGCAGCA      360

GCCTGTCGCT GGCCGTGCCC CCAGGCCCCC TCAGCTTTGA GGCGCTGCTC GCCCAGGTGG      420

GGGCGCTGGG CGGCGGCCAG CAGCTGCAGC TCGGCCTCTG CTGCCTGCCG GTGCTCTTCG      480

TGGCTCTGGG C ATG GCC TCG GAC CCC ATC TTC ACG CTG GCG CCC CCG CTG      530
            Met Ala Ser Asp Pro Ile Phe Thr Leu Ala Pro Pro Leu
             1              5                  10

CAT TGC CAC TAC GGG GCC TTC CCC CCT AAT GCC TCT GGC TGG GAG CAG      578
His Cys His Tyr Gly Ala Phe Pro Pro Asn Ala Ser Gly Trp Glu Gln
     15                  20                  25

CCT CCC AAT GCC AGC GGC GTC AGC GTC GCC AGC GCT GCC CTA GCA GCC      626
Pro Pro Asn Ala Ser Gly Val Ser Val Ala Ser Ala Ala Leu Ala Ala
 30                  35                  40                  45

AGC GCC GCC AGC CGT GTC GCC ACC AGT ACC GAC CCC TCG TGC AGC GGC      674
Ser Ala Ala Ser Arg Val Ala Thr Ser Thr Asp Pro Ser Cys Ser Gly
                 50                  55                  60

TTC GCC CCG CCG GAC TTC AAC CAT TGC CTC AAG GAT TGG GAC TAT AAT      722
Phe Ala Pro Pro Asp Phe Asn His Cys Leu Lys Asp Trp Asp Tyr Asn
             65                  70                  75

GGC CTT CCT GTG CTC ACC ACC AAC GCC ATC GGC CAG TGG GAT CTG GTG      770
Gly Leu Pro Val Leu Thr Thr Asn Ala Ile Gly Gln Trp Asp Leu Val
         80                  85                  90

TGT GAC CTG GGC TGG CAG GTG ATC CTG GAG CAG ATC CTC TTC ATC TTG      818
Cys Asp Leu Gly Trp Gln Val Ile Leu Glu Gln Ile Leu Phe Ile Leu
 95                 100                 105

GGC TTT GCC TCC GGC TAC CTG TTC CTG GGT TAC CCC GCA GAC AGA TTT      866
Gly Phe Ala Ser Gly Tyr Leu Phe Leu Gly Tyr Pro Ala Asp Arg Phe
110                 115                 120                 125

GGC CGT CGC GGG ATT GTG CTG CTG ACC TTG GGG CTG GTG GGC CCC TGT      914
Gly Arg Arg Gly Ile Val Leu Leu Thr Leu Gly Leu Val Gly Pro Cys
                130                 135                 140

GGA GTA GGA GGG GCT GCT GCA GGC TCC TCC ACA GGC GTC ATG GCC CTC      962
Gly Val Gly Gly Ala Ala Ala Gly Ser Ser Thr Gly Val Met Ala Leu
            145                 150                 155

CGA TTC CTC TTG GGC TTT CTG CTT GCC GGT GTT GAC CTG GGT GTC TAC     1010
Arg Phe Leu Leu Gly Phe Leu Leu Ala Gly Val Asp Leu Gly Val Tyr
        160                 165                 170

CTG ATG CGC CTG GAG CTG TGC GAC CCA ACC CAG AGG CTT CGG GTG GCC     1058
Leu Met Arg Leu Glu Leu Cys Asp Pro Thr Gln Arg Leu Arg Val Ala
    175                 180                 185

CTG GCA GGG GAG TTG GTG GGG GTG GGA GGG CAC TTC CTG TTC CTG GGC     1106
Leu Ala Gly Glu Leu Val Gly Val Gly Gly His Phe Leu Phe Leu Gly
190                 195                 200                 205

CTG GCC CTT GTC TCT AAG GAT TGG CGA TTC CTA CAG CGA ATG ATC ACC     1154
Leu Ala Leu Val Ser Lys Asp Trp Arg Phe Leu Gln Arg Met Ile Thr
                210                 215                 220

GCT CCC TGC ATC CTC TTC CTG TTT TAT GGC TGG CCT GGT TTG TTC CTG     1202
Ala Pro Cys Ile Leu Phe Leu Phe Tyr Gly Trp Pro Gly Leu Phe Leu
            225                 230                 235

GAG TCC GCA CGG TGG CTG ATA GTG AAG CGG CAG ATT GAG GAG GCT CAG     1250
Glu Ser Ala Arg Trp Leu Ile Val Lys Arg Gln Ile Glu Glu Ala Gln
        240                 245                 250

TCT GTG CTG AGG ATC CTG GCT GAG CGA AAC CGG CCC CAT GGG CAG ATG     1298
```

```
Ser Val Leu Arg Ile Leu Ala Glu Arg Asn Arg Pro His Gly Gln Met
    255                 260                 265

CTG GGG GAG GAG GCC CAG GAG GCC CTG CAG GAC CTG GAG AGC TCC ACA      1346
Leu Gly Glu Glu Ala Gln Glu Ala Leu Gln Asp Leu Glu Ser Ser Thr
270                 275                 280                 285

CTG TAACCACTGG GTCTGGGCTC CATCCTGCGC CCAAAGACAT CCACCCAGAC           1399
Leu

CTCATTATTT CTTGCTCTAT CATTCTGTTT CAATAAAGAC ATTTGGAATA AACGAGCATA    1459

AAAAAAAAAA AAAAAAAAA AAAAAAAAAA A                                    1490

(2) INFORMATION FOR SEQ ID NO:4:

(i) SEQUENCE CHARACTERISTICS:
        (A) LENGTH: 286 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

Met Ala Ser Asp Pro Ile Phe Thr Leu Ala Pro Pro Leu His Cys His
1                   5                   10                  15

Tyr Gly Ala Phe Pro Pro Asn Ala Ser Gly Trp Glu Gln Pro Pro Asn
                20                  25                  30

Ala Ser Gly Val Ser Val Ala Ser Ala Ala Leu Ala Ala Ser Ala Ala
            35                  40                  45

Ser Arg Val Ala Thr Ser Thr Asp Pro Ser Cys Ser Gly Phe Ala Pro
        50                  55                  60

Pro Asp Phe Asn His Cys Leu Lys Asp Trp Asp Tyr Asn Gly Leu Pro
65                  70                  75                  80

Val Leu Thr Thr Asn Ala Ile Gly Gln Trp Asp Leu Val Cys Asp Leu
                85                  90                  95

Gly Trp Gln Val Ile Leu Glu Gln Ile Leu Phe Ile Leu Gly Phe Ala
            100                 105                 110

Ser Gly Tyr Leu Phe Leu Gly Tyr Pro Ala Asp Arg Phe Gly Arg Arg
        115                 120                 125

Gly Ile Val Leu Leu Thr Leu Gly Leu Val Gly Pro Cys Gly Val Gly
130                 135                 140

Gly Ala Ala Ala Gly Ser Ser Thr Gly Val Met Ala Leu Arg Phe Leu
145                 150                 155                 160

Leu Gly Phe Leu Leu Ala Gly Val Asp Leu Gly Val Tyr Leu Met Arg
                165                 170                 175

Leu Glu Leu Cys Asp Pro Thr Gln Arg Leu Arg Val Ala Leu Ala Gly
            180                 185                 190

Glu Leu Val Gly Val Gly Gly His Phe Leu Phe Leu Gly Leu Ala Leu
        195                 200                 205

Val Ser Lys Asp Trp Arg Phe Leu Gln Arg Met Ile Thr Ala Pro Cys
210                 215                 220

Ile Leu Phe Leu Phe Tyr Gly Trp Pro Gly Leu Phe Leu Glu Ser Ala
225                 230                 235                 240

Arg Trp Leu Ile Val Lys Arg Gln Ile Glu Glu Ala Gln Ser Val Leu
                245                 250                 255

Arg Ile Leu Ala Glu Arg Asn Arg Pro His Gly Gln Met Leu Gly Glu
            260                 265                 270
```

```
Glu Ala Gln Glu Ala Leu Gln Asp Leu Glu Ser Ser Thr Leu
        275                 280                 285

(2) INFORMATION FOR SEQ ID NO:5:

(i) SEQUENCE CHARACTERISTICS:
        (A) LENGTH: 1411 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...966

(xi) SEQUENCE DESCRIPTION: SEQ ID NO:5:

GTC GAC CCA CGC GTC CGG GGC CTG GCC CTT GTC TCT AAG GAC TGG CGG        48
Val Asp Pro Arg Val Arg Gly Leu Ala Leu Val Ser Lys Asp Trp Arg
 1               5                  10                  15

TTC CTG CAG CGA ATG ATC ACC GCT CCT TGC ATC CTC TTC CTG TTT TAT        96
Phe Leu Gln Arg Met Ile Thr Ala Pro Cys Ile Leu Phe Leu Phe Tyr
             20                  25                  30

GGC TGG CCC GGT CTG TTT CTG GAC TCC GCA CGG TGG CTG ATA GTG AAA       144
Gly Trp Pro Gly Leu Phe Leu Asp Ser Ala Arg Trp Leu Ile Val Lys
         35                  40                  45

CGG CAG ATT GAG GAA GCC CAG TCT GTG CTG AGG ATC CTG GCT GAG CGA       192
Arg Gln Ile Glu Glu Ala Gln Ser Val Leu Arg Ile Leu Ala Glu Arg
     50                  55                  60

AAC CGG CCC CAT GGC CAG ATG CTG GGA GAA GAG GCC CAG GAA GCC CTG       240
Asn Arg Pro His Gly Gln Met Leu Gly Glu Glu Ala Gln Glu Ala Leu
 65                  70                  75                  80

CAG GAG CTG GAG AAT ACC TGT CCT CTC CCC ACA ACG TCC ACC TTT TCC       288
Gln Glu Leu Glu Asn Thr Cys Pro Leu Pro Thr Thr Ser Thr Phe Ser
                 85                  90                  95

TTC GCC TCC CTC CTC AAC TAC CGA AAC ATC TGG AAA AAT CTG CTT ATC       336
Phe Ala Ser Leu Leu Asn Tyr Arg Asn Ile Trp Lys Asn Leu Leu Ile
            100                 105                 110

CTG GGC TTC ACC AAC TTT ATC GCC CAT GCC ATT CGC CAC TGC TAC CAG       384
Leu Gly Phe Thr Asn Phe Ile Ala His Ala Ile Arg His Cys Tyr Gln
        115                 120                 125

CCT GTG GGA GGA GGA GGG AGC CCA TCA GAC TTC TAC TTG TGC TCT CTT       432
Pro Val Gly Gly Gly Gly Ser Pro Ser Asp Phe Tyr Leu Cys Ser Leu
    130                 135                 140

CTG GCC AGC GGC ACA GCA GCC CTG GCC TGC GTC TTC CTG GGG GTG ACC       480
Leu Ala Ser Gly Thr Ala Ala Leu Ala Cys Val Phe Leu Gly Val Thr
145                 150                 155                 160

GTG GAC CGT TTC GGC CGT CGG GGC ATC CTG CTT CTC TCA ATG ACT CTC       528
Val Asp Arg Phe Gly Arg Arg Gly Ile Leu Leu Leu Ser Met Thr Leu
                165                 170                 175

ACG GGG ATT GCA TCC CTG GTC TTG CTG GGC CTG TGG GAT TAT CTG AAC       576
Thr Gly Ile Ala Ser Leu Val Leu Leu Gly Leu Trp Asp Tyr Leu Asn
            180                 185                 190

GAT GCT GCC ATC ACA ACC TTC TCG GTC CTC GGA CTC TTC TCC TCC CAA       624
Asp Ala Ala Ile Thr Thr Phe Ser Val Leu Gly Leu Phe Ser Ser Gln
        195                 200                 205

GCT TCT GCT ATC CTC AGT ACC CTC CTT GCT GCT GAA GTC ATC CCC ACC       672
Ala Ser Ala Ile Leu Ser Thr Leu Leu Ala Ala Glu Val Ile Pro Thr
    210                 215                 220

ACT GTC CGG GGC CGT GGC CTG GGC CTT ATC ATG GCA CTT GGG GCG CTT       720
Thr Val Arg Gly Arg Gly Leu Gly Leu Ile Met Ala Leu Gly Ala Leu
225                 230                 235                 240
```

```
GGA GGG CTG AGC TGT CCA GCT CAG CGC CTC CAC ATG GGC CAT GGA GCT    768
Gly Gly Leu Ser Cys Pro Ala Gln Arg Leu His Met Gly His Gly Ala
            245                 250                 255

TTC CTG CAG CAT GTG GTA CTG GCG GCC TGT GCC CTC CTC TGC ATC CTT    816
Phe Leu Gln His Val Val Leu Ala Ala Cys Ala Leu Leu Cys Ile Leu
            260                 265                 270

AGC ATC ATG CTG CTG CCA GAG ACC AAG CGC AAG CTT CTG CCA GAG GTA    864
Ser Ile Met Leu Leu Pro Glu Thr Lys Arg Lys Leu Leu Pro Glu Val
            275                 280                 285

CTC CGG GAT GGG GAA CTG TGC CGT CGG CCT TCC CTG CTG AGG CAG CCA    912
Leu Arg Asp Gly Glu Leu Cys Arg Arg Pro Ser Leu Leu Arg Gln Pro
            290                 295                 300

CCT CCT AAC CGC TGT GAC CAT GTC CCC CTG CTA GCC ACT CCT AAT CCT    960
Pro Pro Asn Arg Cys Asp His Val Pro Leu Leu Ala Thr Pro Asn Pro
305                 310                 315                 320

GCC CTC TAAGCAGCCT CTGAGCCTGG TGGGAGGCTG GCCATTTAGA AAGGTGACGG    1016
Ala Leu
AGGGCTGGCT AGCAAGATAG ACGGAGAGGC AAGGCCACCC TGTACATACA AAAGGCTCCA    1076

AGGCGCCTCA CGCCATCTAG GAGAGCTCAG AGTGCCATTC CCAACCCCCT CTCCTCCCCG    1136

CTGCTTTCTG TTCACTTCAT CAGCAAGAGT CAGGACGGGG ATAGCATCTC GCTATAACCG    1196

TTAGGTCTGG GATCCATCCT ATGCCCAAAG ACATTTTCCC AGACCTTGCT CTTTCTCGCT    1256

CTTCATTCTG TTTCAATAAA AGACATTTTG AATAAATGAG CATTTCATAG CCTGGGAAAA    1316

AAAAAAAAAA AAAAAAAAAA AAAAAAAAAA AAAAAAAAAA AAAAAAAAAA AAAAAAAAAA    1376

AAAAAAAAAA AAAAAAAAAA AAAAAGGGCG GCCGC                              1411

(2) INFORMATION FOR SEQ ID NO:6:

(i) SEQUENCE CHARACTERISTICS:
        (A) LENGTH: 322 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:6:

Val Asp Pro Arg Val Arg Gly Leu Ala Leu Val Ser Lys Asp Trp Arg
 1               5                  10                  15

Phe Leu Gln Arg Met Ile Thr Ala Pro Cys Ile Leu Phe Leu Phe Tyr
                20                  25                  30

Gly Trp Pro Gly Leu Phe Leu Asp Ser Ala Arg Trp Leu Ile Val Lys
            35                  40                  45

Arg Gln Ile Glu Glu Ala Gln Ser Val Leu Arg Ile Leu Ala Glu Arg
        50                  55                  60

Asn Arg Pro His Gly Gln Met Leu Gly Glu Glu Ala Gln Glu Ala Leu
 65                 70                  75                  80

Gln Glu Leu Glu Asn Thr Cys Pro Leu Pro Thr Thr Ser Thr Phe Ser
                85                  90                  95

Phe Ala Ser Leu Leu Asn Tyr Arg Asn Ile Trp Lys Asn Leu Leu Ile
                100                 105                 110

Leu Gly Phe Thr Asn Phe Ile Ala His Ala Ile Arg His Cys Tyr Gln
            115                 120                 125

Pro Val Gly Gly Gly Ser Pro Ser Asp Phe Tyr Leu Cys Ser Leu
        130                 135                 140

Leu Ala Ser Gly Thr Ala Ala Leu Ala Cys Val Phe Leu Gly Val Thr
```

-continued

```
                145                 150                 155                 160
Val Asp Arg Phe Gly Arg Arg Gly Ile Leu Leu Ser Met Thr Leu
                    165                 170                 175
Thr Gly Ile Ala Ser Leu Val Leu Gly Leu Trp Asp Tyr Leu Asn
                    180                 185                 190
Asp Ala Ala Ile Thr Thr Phe Ser Val Leu Gly Leu Phe Ser Ser Gln
                    195                 200                 205
Ala Ser Ala Ile Leu Ser Thr Leu Leu Ala Ala Glu Val Ile Pro Thr
            210                 215                 220
Thr Val Arg Gly Arg Gly Leu Gly Leu Ile Met Ala Leu Gly Ala Leu
225                 230                 235                 240
Gly Gly Leu Ser Cys Pro Ala Gln Arg Leu His Met Gly His Gly Ala
                    245                 250                 255
Phe Leu Gln His Val Val Leu Ala Ala Cys Ala Leu Leu Cys Ile Leu
                    260                 265                 270
Ser Ile Met Leu Leu Pro Glu Thr Lys Arg Lys Leu Leu Pro Glu Val
                    275                 280                 285
Leu Arg Asp Gly Glu Leu Cys Arg Arg Pro Ser Leu Leu Arg Gln Pro
            290                 295                 300
Pro Pro Asn Arg Cys Asp His Val Pro Leu Leu Ala Thr Pro Asn Pro
305                 310                 315                 320
Ala Leu
```

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:7:

```
Gly Tyr Xaa Xaa Asp Arg Xaa Gly Arg Arg
1               5                   10
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:8:

```
Gly Tyr Pro Ala Asp Arg Phe Gly Arg Arg
1               5                   10
```

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:9:

```
Ile Ser Lys Met Phe
1               5
```

(2) INFORMATION FOR SEQ ID NO:10:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:10:

```
Arg Xaa Leu Xaa Gly Xaa Xaa Leu Ala Xaa Xaa Xaa Xaa Xaa Xaa
 1               5                  10                  15

Xaa Leu Xaa Thr Glu Trp Xaa Xaa Xaa Xaa Xaa Arg
            20                  25
```

(2) INFORMATION FOR SEQ ID NO:11:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:11:

```
Arg Phe Leu Leu Gly Phe Leu Leu Ala Gly Val Asp Leu Gly Val Tyr
 1               5                  10                  15

Leu Met Arg Leu Glu Leu Cys Asp Pro Thr Gln Arg
            20                  25
```

(2) INFORMATION FOR SEQ ID NO:12:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:12:

```
Pro Glu Ser Xaa Arg Trp Leu
 1               5
```

(2) INFORMATION FOR SEQ ID NO:13:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:13:

```
Leu Glu Ser Ala Arg Trp Leu
 1               5
```

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:14:

```
Leu Leu Pro Glu Thr Lys
```

```
(2) INFORMATION FOR SEQ ID NO:15:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:15:

Thr Gln Thr Arg
 1

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:16:

Leu Xaa Asn Xaa Glu Leu Tyr Pro Thr Xaa Xaa Arg Asn Leu Gly
 1               5                  10                  15

(2) INFORMATION FOR SEQ ID NO:17:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:17:

Leu Leu Ala Ala Glu Val Ile Pro Thr Thr Val Arg Gly Arg Gly
 1               5                  10                  15
```

OCT-3 GENE ENCODING TRANSPORTER-LIKE MOLECULES

BACKGROUND OF THE INVENTION

The field of the invention is cellular transporter molecules.

In the course of performing their normal physiological functions, many types of cells, including bacterial cells and those in specialized mammalian tissues such as the liver and kidney, transport a variety of organic molecules across their cell membranes. For example, cells in the proximal tubule of the kidney transport glucose, amino acids, and uric acid across their membranes, and work to eliminate various drugs and toxic substances from the body. All of these molecules are transported across the cell membranes by specialized cellular transporters.

Recently, genes encoding several putative transporters have been identified. These molecules include OCT-1 (organic cation transporter; Grundemann et al., *Nature* 372:549–552, 1994), OCT-2 (Okuda et al., *Biochem. Biophys. Res. Comm.* 224:500–507, 1996), NLT (novel liver-specific transporter; Simonson et al., *J. Cell Sci.* 107:1067–1072, 1994), and NKT (novel kidney-specific transporter; Lopez-Nieto et al., *J. Biol. Chem.* 272:6471–6478, 1997). While the sequences of these transporters are not highly conserved (at the amino acid level, OCT-1 and NLT are only 30% and 35% identical to NKT, respectively), they do exhibit similar transmembrane (TM) domain hydropathy profiles.

SUMMARY OF THE INVENTION

The invention described herein relates to the discovery and characterization of oct-3, a gene encoding a protein that transports molecules across the plasma membranes of biological cells. OCT-3 is highly expressed in the neuronal cells of the brain. Accordingly, altering the expression or activity of OCT-3 (e.g., with small molecules, antisense molecules, or neutralizing antibodies) can alter the concentration of molecules (such as neurotransmitters) that are present within the cell or in the extracellular spaces around the cell (i.e., on either side of the plasma membrane). Altering the concentrations of these molecules in patients afflicted with certain conditions, including neurodegenerative diseases, behavioral disorders, and eating or sleep disorders, can provide relief from the symptoms associated with these conditions.

More specifically, the invention features an isolated nucleic acid molecule (i.e., a nucleic acid molecule that is separated from the 5' and 3' coding sequences with which it is immediately contiguous in the naturally occurring genome of an organism) that encodes an OCT-3 polypeptide. As used herein, an OCT-3 polypeptide is a polypeptide that: (1) is expressed in the plasma membrane of a biological cell (e.g., a cell in the kidney, liver, or brain), (2) contains TM domains, and (3) when functioning normally, transports organic molecules across the plasma membrane. Preferably, the OCT-3 polypeptide has at least 6 transmembrane domains (e.g., 6, 8, or 10 TM domains), and more preferably, has at least 12 TM domains. The OCT-3 polypeptide can be a mammalian polypeptide, i.e., a polypeptide normally expressed by the cells of a mammal, such as a human. In the event the OCT-3 polypeptide is human, it can have the sequence shown in SEQ ID NO:2 or SEQ ID NO:4, or it can be encoded by nucleic acid molecules having the sequence shown in SEQ ID NO:1 or SEQ ID NO:3. However, the invention is not limited to nucleic acid molecules and polypeptides that are identical to those SEQ ID Nos. For example, the invention includes nucleic acid molecules which encode splice variants, allelic variants or mutant forms of OCT-3 as well as the proteins encoded by such nucleic acid molecules. Also within the invention are nucleic acid molecules that hybridize under stringent conditions to a nucleic acid molecule having the sequence of SEQ ID NO:1 or SEQ ID NO:3. As described further below, molecules that are substantially identical to SEQ ID Nos. 1–4 are also encompassed.

The term "substantially pure" as used herein in reference to a given compound (e.g., an OCT-3 polypeptide) means that the compound is substantially free from other compounds, such as those in cellular material, viral material, or culture medium, with which the compound may have been associated (e.g., in the course of production by recombinant DNA techniques or before purification from a natural biological source). When chemically synthesized, a compound of the invention is substantially pure when it is substantially free from the chemical compounds used in the process of its synthesis. Polypeptides or other compounds of interest are substantially free from other compounds when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria. The same rule applies for nucleic acid molecules.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably at least 100 nucleotides (e.g., 150, 200, 250, or 300 nucleotides).

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (e.g., the Sequence Analysis Software Package of the Genetics Computer Group, University of Wisconsin Biotechnology Center, 1710 University Avenue, Madison, Wis. 53705), with the default parameters as specified therein.

The invention also features a host cell that includes an isolated nucleic acid molecule encoding OCT-3 (either alone or in conjunction with a heterologous polypeptide, such as a detectable marker), or a nucleic acid vector that contains a sequence encoding OCT-3 (again, with or without a heterologous polypeptide). The vector can be an expression vector, and can include a regulatory element.

An antibody that specifically binds an OCT-3 polypeptide is also within the scope of the present invention and is useful, for example, to detect OCT-3 in a biological sample, or to alter the activity of OCT-3. For example, OCT-3 can be detected in a biological sample by contacting the sample with an antibody that specifically binds OCT-3 under conditions that allow the formation of an OCT-3-antibody complex and detecting the complex, if present, as an indication of the presence of OCT-3 in the sample. The use of an antibody in a treatment regime, where it can alter the activity of OCT-3, is discussed further below.

An antibody of the invention can be a monoclonal, polyclonal, or engineered antibody that specifically binds OCT-3 (as described more fully below). An antibody that "specifically binds" to a particular antigen, for example, an OCT-3 polypeptide of the invention, will not substantially recognize or bind to other molecules in a sample, such as a biological sample, that includes OCT-3.

Given that an object of the present invention is to alter the expression or activity of OCT-3 in vivo, a pharmaceutical composition containing, for example, an isolated nucleic acid molecule encoding OCT-3 (or a fragment thereof), a nucleic acid molecule that is antisense to OCT-3 (i.e., that has a sequence that is the reverse and complement of a portion of the coding strand of an OCT-3 gene), an OCT-3 polypeptide, or an antibody, small molecule, or other compound that specifically binds an OCT-3 polypeptide is also a feature of the invention.

The discovery and characterization of oct-3 and the polypeptide it encodes makes it possible to determine whether a given disorder is associated with aberrant expression of oct-3 (meaning expression at the level of gene transcription or mRNA translation) or activity of OCT-3. For example, one can diagnose a patient as having a disorder associated with aberrant expression of oct-3 by measuring oct-3 expression in a biological sample obtained from the patient. An increase or decrease in oct-3 expression in the biological sample, compared with oct-3 expression in a control sample (e.g., a sample of the same tissue collected from one or more healthy individuals) indicates that the patient has a disorder associated with aberrant expression of oct-3. Similarly, one can diagnose a patient as having a disorder associated with aberrant activity of OCT-3 by measuring OCT-3 activity in a biological sample obtained from the patient. An increase or decrease in OCT-3 activity in the biological sample, compared with OCT-3 activity in a control sample, indicates that the patient has a disorder associated with aberrant activity of OCT-3. The techniques required to measure gene expression or polypeptide activity are well known to those of ordinary skill in the art.

In addition to diagnostic methods, such as those described above, the present invention encompasses methods and compositions for typing and evaluating the prognosis, appropriate treatment, and treatment effectiveness of disorders associated with inappropriate expression of oct-3 or inappropriate activity of OCT-3. For example, the nucleic acid molecules of the invention can be used as probes to classify cells in terms of their level of oct-3 expression, or as primers for diagnostic PCR analysis in which mutations, allelic variations, and regulatory defects in the oct-3 gene can be detected. Similarly, those of ordinary skill in the art can use routine techniques to identify inappropriate activity of OCT-3, which can be observed in a variety of forms. For example, inappropriate activity can take the form of an alteration in the rate with which an OCT-3 transporter moves molecules across the plasma membrane, or a difference in the type of molecule that is transported. Diagnostic kits for the practice of such methods are also provided.

The invention further encompasses transgenic animals that express OCT-3 and recombinant "knock-out" animals that fail to express OCT-3. These animals can serve as new and useful models of disorders in which oct-3 is misexpressed.

The invention also features antagonists and agonists of OCT-3 that can inhibit or enhance, respectively, one or more of the biological activities of OCT-3. Suitable antagonists can include small molecules (i.e., molecules with a molecular weight below about 500), large molecules (i.e., molecules with a molecular weight above about 500), antibodies that specifically bind and "neutralize" OCT-3 (as described below), and nucleic acid molecules that interfere with transcription or translation of OCT-3 (e.g., antisense nucleic acid molecules and ribozymes). Agonists of OCT-3 also include small and large molecules, and antibodies other than neutralizing antibodies.

The invention also features molecules that can increase or decrease the expression of oct-3 (e.g., by altering transcription or translation). Small molecules (as defined above), large molecules (as defined above), and nucleic acid molecules (e.g., antisense and ribozyme molecules) can be used to inhibit the expression of oct-3. Other types of nucleic acid molecules (e.g., molecules that bind to oct-3 transcriptional regulatory sequences) can be used to increase the expression of oct-3.

Compounds that modulate the expression of oct-3 in a cell can be identified by comparing the level of expression of oct-3 in the presence of a selected compound with the level of expression of oct-3 in the absence of that compound. A difference in the level of oct-3 expression indicating that the selected compound modulates the expression of oct-3 in the cell. A comparable test for compounds that modulate the activity of OCT-3 can be carried out by comparing the level of OCT-3 activity in the presence and absence of the compound.

Patients who have a neurological disorder mediated by abnormal OCT-3 activity can be treated by administration of a compound that alters the expression of OCT-3 or the activity of OCT-3. When the objective is to decrease expression or activity, the compound administered can be an oct-3 antisense oligonucleotide or an antibody, such as a neutralizing antibody, that specifically binds OCT-3, respectively.

A wide variety of OCT-3 mediated neurological disorders are amenable to treatment according to the methods set forth herein. For example, the neurological disorder can be a neurodegenerative disease, such as Parkinson's Disease, Huntington's Disease, or Alzheimer's Disease. Alternatively, the neurological disorder can be characterized by abnormal behavior or mood disorders. For example, the patient may suffer from depression, anxiety, or schizophrenia. A patient who has a sleep disorder or a weight disorder, such as a patient who is obese or who is suffering from a wasting disorder (as often occurs in the event of AIDS) can also be treated by administration of a compound that alters the expression of oct-3 or the activity of OCT-3. A detailed description of these methods of treatment is set forth below.

The preferred methods and materials are described below in examples which are meant to illustrate, not limit, the invention. Skilled artisans will recognize methods and materials that are similar or equivalent to those described herein, and that can be used in the practice or testing of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In addition, the materials, methods, and examples are illustrative only and are not intended to be limiting.

Other features and advantages of the invention will be apparent from the detailed description, and from the claims.

BRIEF DESCRIPTION OF THE DRAWINGS

FIG. 1 is a depiction of a human oct-3 nucleotide sequence (including 3' and 5' non-translated sequence; SEQ ID NO:1) that encodes an OCT-3 polypeptide with 12 transmembrane domains (SEQ ID NO:2).

FIG. 2 is a depiction of a human oct-3 nucleotide sequence (including 3' and 5' non-translated sequence; SEQ ID NO:3) that encodes an OCT-3 polypeptide with 6 TM domains (SEQ ID NO:4).

FIG. 3 is a depiction of a rat oct-3 nucleotide sequence (SEQ ID NO:5) encoding a rat OCT-3 polypeptide (SEQ ID NO: 6). This polypeptide does not appear to be full-length.

FIGS. 4A–4E are representations of regions of amino acids in the OCT-3 polypeptide (SEQ ID NO:2) that conform to consensus sequences derived from polypeptides in the OCT family. Alternative residues for each consensus sequence are shown on the uppermost line. The sequences shown in FIG. 4A are found in the second transmembrane domain and continue between the second and third TM domains; the sequences shown in FIG. 4B are found in the in the fourth transmembrane domain and continue between the fourth and fifth TM domains; the sequences shown in FIG. 4C are found between the sixth and seventh TM domains; the sequences shown in FIG. 4D are found C-terminal to the twelfth TM domain; and the sequences shown in FIG. 4E are found in the tenth transmembrane domain and continue between the tenth and eleventh TM domains.

DETAILED DESCRIPTION

As described above, the nucleic acid molecules of the invention and the polypeptides they encode (e.g., OCT-3 polypeptides or fragments thereof) can be used directly as diagnostic and therapeutic agents, or they can be used to generate antibodies or identify small molecules that, in turn, are clinically useful. In addition, oct-3 nucleic acid molecules are useful in genetic mapping, to identify the chromosomal location of oct-3, and as tissue-specific (e.g., neuronal-specific) markers. Accordingly, expression vectors containing the nucleic acid molecules of the invention, cells transfected with these vectors, the polypeptides expressed, and antibodies generated, against either the entire polypeptide or an antigenic fragment thereof, are among the preferred embodiments. These embodiments and their clinical application are described further below.

I. Nucleic Acid Molecules Encoding OCT-3

The oct-3 nucleic acid molecules of the invention can be cDNA, genomic DNA, synthetic DNA, or RNA, and can be double-stranded or single-stranded. In the event the nucleic acid molecule is single-stranded, it can be either a sense or an antisense strand. Fragments of these molecules are also considered within the scope of the invention, and can be produced, for example, by the polymerase chain reaction (PCR), or generated by treating a longer fragment (e.g., a full-length oct-3 gene sequence) with one or more restriction endonucleases. Similarly, a full-length oct-3 RNA molecule, or a fragment thereof, can be produced by in vitro transcription. The isolated nucleic acid molecule of the invention can encode a fragment of OCT-3 that is not found as such in the natural state. Although nucleic acid molecules encoding any given fragment of OCT-3 are within the scope of the invention, fragments that retain the biological activity of OCT-3 (as assessed below) are preferred.

The nucleic acid molecules of the invention encompass recombinant molecules, such as those in which a nucleic acid molecule (e.g., an isolated nucleic acid molecule encoding OCT-3, or a fragment thereof) is incorporated: (1) into a vector (e.g., a plasmid or viral vector), (2) into the genome of a heterologous cell, or (3) into the genome of a homologous cell, at a position other than the natural chromosomal location. Recombinant nucleic acid molecules, transgenic animals, and uses therefor are discussed further below.

The nucleic acid molecules of the invention can contain naturally occurring sequences, or sequences that differ from those that occur naturally, but, due to the degeneracy of the genetic code, encode the same polypeptide (e.g., the polypeptides of SEQ ID NO:2 or SEQ ID NO:4). In addition, the nucleic acid molecules of the invention are not limited to those that encode the amino acid residues of the OCT-3 polypeptide as shown is SEQ ID NOs:1 and 2; they can also include some or all of the non-coding sequences that lie upstream or downstream from an oct-3 coding sequence, a heterologous regulatory element, or a sequence encoding a heterologous polypeptide (e.g., a reporter gene). Regulatory elements and reporter genes are discussed further below.

The nucleic acid molecules of the invention can be synthesized (for example, by phosphoramidite-based synthesis) or obtained from a biological cell, such as the cell of a mammal. Thus, the nucleic acids can be those of a human, mouse, rat, guinea pig, cow, sheep, goat, horse, pig, rabbit, monkey, dog, or cat. Combinations or modifications of the nucleotides within these types of nucleic acid molecules are also encompassed.

In the event the nucleic acid molecules of the invention encode or act as antisense molecules, they can be used, for example, to regulate translation of oct-3 mRNA. Techniques associated with detection of nucleic acid sequences or regulation of their expression are well known to persons of ordinary skill in the art, and can be used in the context of the present invention to diagnose or treat disorders associated with aberrant oct-3 expression. However, aberrent expression of oct-3 (or aberrant activity of OCT-3) is not a prerequisite for treatment according to the methods of the invention; the molecules of the invention (including the nucleic acid molecules described here) are expected to be useful in improving the symptoms associated with a variety of medical conditions (particularly neurological disorders) regardless of whether or not the expression of oct-3 (or the activity of OCT-3) is detectably aberrant. Nucleic acid molecules are discussed further below in the context of their clinical utility.

The invention also encompasses nucleic acid molecules that encode other members of the OCT-3 family. Such nucleic acid molecules will be readily identified by the ability to hybridize under stringent conditions to a nucleic acid molecule encoding an OCT-3 polypeptide (SEQ ID NOs:1 and 3). The cDNA sequences described herein (SEQ ID NOs:1, 3, and 5) can be used to identify these nucleic acids, which include, for example, nucleic acids that encode homologous polypeptides in other species, splice variants of the oct-3 gene in humans or other mammals, allelic variants of the oct-3 gene in humans or other mammals, and mutant forms of the oct-3 gene in humans or other mammals.

The preferred class of nucleic acid molecules that hybridize to SEQ ID NOs:1 and 3 are nucleic acid molecules that encode human allelic variants of OCT-3. There are two major classes of such variants: active allelic variants, naturally occurring variants of SEQ ID NOs:2 and 4 that have the ability to act as a transporter and non-active allelic variants, naturally occurring allelic variants of SEQ ID NOs:2 and 4 that are unable to function as a transporter. Active allelic variants can be used as an equivalent for an OCT-3 protein having the amino acid sequence of SEQ ID NOs:2 or 4 as described herein whereas nonactive allelic variants can be used in methods of disease diagnosis and as a therapeutic target.

The invention features methods of detecting and isolating such nucleic acid molecules. Using these methods, a sample (e.g., a nucleic acid library, such as a cDNA or genomic library) is contacted (or "screened") with an oct-3-specific probe (e.g., a fragment of SEQ ID NO:1 that is at least 17 nucleotides long). The probe will selectively hybridize to nucleic acids encoding related polypeptides (or to complementary sequences thereof). The term "selectively hybridize" is used to refer to an event in which a probe binds to nucleic acid molecules encoding OCT-3 (or to complementary sequences thereof) to a detectably greater extent than to nucleic acids encoding other polypeptides, particularly other types of transporter molecules (or to complementary sequences thereof). The probe, which can contain at least 17 nucleotides (e.g., 18, 20, 25, 50, 100, 150, or 200 nucleotides) can be produced using any of several standard methods (see, e.g., Ausubel et al., "Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify an oct-3-specific nucleic acid sequence (for example, a nucleic acid encoding one of the transmembrane domains) that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the double helix). Complete complementarity between the hybridizing regions is not required in order for a duplex to form; it is only necessary that the number of paired bases is sufficient to maintain the duplex under the hybridization conditions used.

Typically, hybridization conditions initially used to identify related genes are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (e.g., room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (e.g., the content of purine-like nucleotides versus the content of pyrimidine-like nucleotides) and the type of nucleic acid (e.g., DNA or RNA) affect hybridization. An additional consideration is whether one of the nucleic acids is immobilized (e.g., on a filter).

An example of a progression from lower to higher stringency conditions is the following, where the salt content is given as the relative abundance of SSC (a salt solution containing sodium chloride and sodium citrate; 2× SSC is 10-fold more concentrated than 0.2× SSC). Nucleic acid molecules are hybridized at 42° C. in 2× SSC/0.1% SDS (sodium dodecylsulfate; a detergent) and then washed in 0.2× SSC/0.1% SDS at room temperature (for conditions of low stringency); 0.2× SSC/0.1% SDS at 42° C. (for conditions of moderate stringency); and 0.1× SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

A second set of conditions that are considered "stringent conditions" are those in which hybridization is carried out at 50° C. in Church buffer (7% SDS, 0.5% NaHPO$_4$, 1 M EDTA, 1% BSA) and washing is carried out at 50° C. in 2× SSC.

Preferably, nucleic acid molecules of the invention that are defined by their ability to hybridize with SEQ ID Nos. 1, 3, or 5 under stringent conditions will have additional features in common with oct-3. For example, the nucleic acid molecules identified by hybridization may have a similar, or identical, expression profile as the oct-3 molecules described herein, or may encode a polypeptide having one or more of the biological activities possessed by OCT-3.

Once detected, the nucleic acid molecules can be isolated by any of a number of standard techniques (see, e.g., Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing oct-3 or oct-3-related coding sequences and/or their complements (i.e., "antisense" sequence) and fragments thereof; (b) expression vectors that contain any of the foregoing oct-3-related sequences operatively associated with a regulatory element (examples of which are given below) that directs the expression of the coding sequences; (c) expression vectors containing, in addition to sequences encoding an OCT-3 polypeptide, nucleic acid sequences that are unrelated to nucleic acid sequences encoding OCT-3, such as molecules encoding a reporter or marker; and (d) genetically engineered host cells that contain any of the foregoing expression vectors, and thereby express the nucleic acid molecules of the invention in the host cell. The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors.

Additionally, the OCT-3 encoding nucleic acid molecules of the present invention can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotrarisferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, a chimeric or hybrid polypeptide of the invention will include a first portion and a second portion; the first portion being an OCT-3 polypeptide or a fragment thereof (preferably a biologically active fragment) and the second portion being, for example, the reporter described above or an immunoglobulin constant region.

The expression systems that can be used for purposes of the invention include, but are not limited to, microorganisms such as bacteria (e.g., *E. coli* and *B. subtilis*) transformed with recombinant bacteriophage DNA, plasmid DNA, or cosmid DNA expression vectors containing the nucleic acid molecules of the invention; yeast (e.g., Saccharomyces and Pichia) transformed with recombinant yeast expression vectors containing the nucleic acid molecules of the invention (preferably containing a nucleic acid sequence encoding human OCT-3 (such as the sequence of SEQ ID NO:1 or SEQ ID NO:3)); insect cell systems infected with recombinant virus expression vectors (e.g., baculovirus) containing a nucleic acid molecule of the invention; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing oct-3 nucleotide sequences; or mammalian cell systems (e.g., COS, CHO, BHK, 293, VERO, HeLa, MDCK, WI38, and NIH 3T3 cells) harboring recombinant expression constructs containing promoters derived from the genome of mammalian cells (e.g., the metallothionein promoter) or from mammalian viruses (e.g., the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing OCT-3 polypeptides or for raising antibodies to those polypeptides, vectors that are capable of directing the expression of high levels of fusion protein products that are readily purified may be desirable. Such vectors include, but are not limited to, the *E. coli* expression vector pUR278 (Ruther et al., *EMBO J.* 2:1791, 1983), in which the coding sequence of the insert may be ligated individually into the vector in frame with the lacZ coding region so that a fusion protein is produced; pIN vectors (Inouye and Inouye, *Nucleic Acids Res.* 13:3101–3109, 1985; Van Heeke and Schuster, *J. Biol. Chem.* 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) can be used as a vector to express foreign genes. The virus grows in *Spodoptera frugiperda* cells. The coding sequence of the insert may be cloned individually into non-essential regions (e.g., the polyhedrin gene) of the virus and placed under control of an AcNPV promoter (e.g., the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., *J. Virol.* 46:584, 1983; and Smith, U.S. Pat. No. 4,215,051).

In mammalian host cells, a number of viral-based expression systems may be utilized. In cases where an adenovirus is used as an expression vector, the nucleic acid molecule of the invention can be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing an oct-3 gene product in infected hosts (e.g., see Logan and Shenk, *Proc. Natl. Acad. Sci. USA* 81:3655–3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted (e.g., the portion encoding the mature form of an OCT-3 protein) endoexogenous translational control signals, including, perhaps, the ATG initiation codon, must be provided.

Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. The mammalian cell types listed above are among those that could serve as suitable host cells.

For long-term, high-yield production of recombinant proteins, stable expression is preferred. For example, cell lines which stably express the OCT-3 sequences described above can be engineered. Rather than using expression vectors that contain viral origins of replication, host cells can be transformed with DNA controlled by appropriate expression control elements (e.g., promoter sequences, enhancer sequences, transcription terminators, polyadenylation sites, etc.), and a selectable marker. Following the introduction of the foreign DNA, engineered cells can be allowed to grow for 1–2 days in an enriched media, and then switched to a selective media. The selectable marker in the recombinant plasmid confers resistance to the selection, and allows cells to stably integrate the plasmid into their chromosomes and grow to form foci which, in turn, can be cloned and expanded into cell lines. This method can advantageously be used to engineer cell lines that express OCT-3. Such engineered cell lines may be particularly useful in screening and evaluating compounds that affect the endogenous activity of the gene product (i.e., OCT-3).

A number of selection systems can be used. For example, the herpes simplex virus thymidine kinase (Wigler, et al., *Cell* 11:223, 1977), hypoxanthine-guanine phosphoribosyltransferase (Szybalska and Szybalski, *Proc. Natl. Acad. Sci. USA* 48:2026, 1962), and adenine phosphoribosyltransferase (Lowy, et al., *Cell* 22:817, 1980) genes can be employed in tk⁻, hgprt⁻ or aprt⁻ cells, respectively. Also, anti-metabolite resistance can be used as the basis of selection for the following genes: dhfr, which confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984).

Alternatively, any OCT-3-containing fusion protein can be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA* 88:8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

As implied by the descriptions above, a host cell is any cell into which (or into an ancestor of which) a nucleic acid encoding a polypeptide of the invention (e.g., an OCT-3 polypeptide) has been introduced by means of recombinant DNA techniques.

II. OCT-3 Polypeptides

The OCT-3 polypeptides described herein are those encoded by any of the nucleic acid molecules described above, and include fragments of OCT-3, mutant forms of OCT-3, active and non-active allelic variants of OCT-3, splice variants of OCT-3, truncated forms of OCT-3, and fusion proteins containing all or a portion of OCT-3. These polypeptides can be prepared for a variety of uses including, but not limited to, the generation of antibodies, as reagents in diagnostic assays, for the identification of other cellular gene products or exogenous compounds that can modulate the activity or expression of OCT-3, and as pharmaceutical reagents useful for the treatment of any disorder in which the associated symptoms are improved by altering the activity of OCT-3.

The terms "protein" and "polypeptide" are used herein to describe any chain of amino acid residues, regardless of length or post-translational modification (e.g., modification by glycosylation or phosphorylation). Thus, the term "OCT-3 polypeptide" includes full-length, naturally occurring OCT-3 polypeptides (that can be purified from tissues in which they are naturally expressed, according to standard biochemical methods of purification), as well as recombinantly or synthetically produced polypeptides that correspond either to a full-length, naturally-occurring OCT-3 polypeptide or to particular domains or portions of such a polypeptide. The term also encompasses mature OCT-3 having an added amino-terminal methionine (useful for expression in prokaryotic cells).

Preferred polypeptides are substantially pure OCT-3 polypeptides that are at least 50% (e.g., 55%, 60%, or 65%), more preferably at least 70% (e.g., 72%, 75%, or 78%), even more preferably at least 80% (e.g., 80%, 85% or 90%), and most preferably at least 95% (e.g., 97% or even 99%) identical to SEQ ID NO:2 or SEQ ID NO:4. Those of ordinary skill in the art are well able to determine the percent identity between two amino acid sequences. Further guidance on this point is provided above. In addition, in FIGS. 4A–4E, regions of amino acid sequence that, along with the TM domains, are conserved between OCT-3 and other members of the OCT family of proteins (OCT-1 and OCT-2) are shown. Thus, if a polypeptide is encoded by a nucleic acid that hybridizes under stringent conditions with the oct-3 sequence disclosed herein and also encodes one or more of the conserved regions present in OCT-3, it will be recognized as an OCT-3 polypeptide and thereby considered within the scope of the present invention.

The invention also encompasses polypeptides that are functionally equivalent to OCT-3. These polypeptides are equivalent to OCT-3 in that they are capable of carrying out one or more of the functions of OCT-3 in a biological system. Polypeptides that are functionally equivalent to OCT-3 can have 20%, 40%, 50%, 75%, 80%, or even 90% of one or more of the biological activities of the full-length, mature human form of OCT-3. Such comparisons are generally based on an assay of biological activity in which equal concentrations of the polypeptides (i.e., an OCT-3 polypeptide disclosed herein and a candidate OCT-3 polypeptide) are used and compared. The comparison can also be based on the amount of the polypeptide required to reach 50% of the maximal biological activity obtainable.

Functionally equivalent proteins can be those, for example, that contain additional or substituted amino acid residues. Substitutions may be made on the basis of similarity in polarity, charge, solubility, hydrophobicity, hydrophilicity, and/or the amphipathic nature of the residues involved. Amino acids that are typically considered to provide a conservative substitution for one another are specified in the Summary of the Invention.

Polypeptides that are functionally equivalent to OCT-3 (SEQ ID NO:2) can be made using random mutagenesis techniques well known to those of ordinary skill in the art (and the resulting mutant OCT-3 polypeptides can be tested for activity). It is more likely, however, that such polypeptides will be generated by site-directed mutagenesis (again using techniques well known to persons of ordinary skill in the art). These polypeptides may have increased functionality or decreased functionality.

To design functionally equivalent polypeptides, it is useful to distinguish between conserved positions and variable positions. This can be done by aligning the sequence of oct-3 cDNAs that were obtained from various organisms. Skilled artisans will recognize that conserved amino acid residues are more likely to be necessary for preservation of function. Thus, it is preferable that conserved residues are not altered.

Mutations within the oct-3 coding sequence can be made to generate variant oct-3 genes that are better suited for expression in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N-X-S or N-X--), and/or an amino acid deletion at the second position of any one or more of such recognition sequences, will prevent glycosylation at the modified tripeptide sequence (see, e.g., Miyajima et al., *EMBO J.* 5:1193, 1986)

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells. In addition, an OCT-3 polypeptide can be fused to GST.

The polypeptides of the invention can be chemically synthesized (e.g., see Creighton, "Proteins: Structures and Molecular Principles," W.H. Freeman & Co., NY, 1983), or, perhaps more advantageously, produced by recombinant DNA technology as described herein. For additional guidance, persons of ordinary skill in the art may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis, Gait, M. J. ("Oligonucleotide Synthesis," IRL Press, Oxford, 1984).

The invention also features polypeptides that interact with OCT-3 (and the genes that encode them) and thereby alter the function or activity of OCT-3. Interacting polypeptides can be identified using methods known to those of ordinary skill in the art. One suitable method is the "two-hybrid system," which detects protein interactions in vivo (Chien et al., *Proc. Natl. Acad. Sci. USA*, 88:9578, 1991). A kit for practicing this method is available from Clontech (Palo Alto, Calif.).

III. Transgenic animals

OCT-3 polypeptides can also be expressed in transgenic animals. Such transgenic animals represent model systems for the study of disorders that are either caused by or exacerbated by misexpression of oct-3, or disorders that can be treated by altering the expression of oct-3 or the activity of OCT-3 (even though the expression or activity is not detectably abnormal). Transgenic animals can also be used for the development of therapeutic agents that modulate the expression of oct-3 or the activity of OCT-3.

Transgenic animals can be farm animals (e.g., pigs, goats, sheep, cows, horses, rabbits, and the like) rodents (such as rats, guinea pigs, and mice), non-human primates (e.g., baboons, monkeys, and chimpanzees), and domestic animals (e.g., dogs and cats). Transgenic mice are especially preferred.

Any technique known in the art can be used to introduce an oct-3 transgene into animals to produce founder lines of transgenic animals. Such techniques include, but are not limited to, pronuclear microinjection (U.S. Pat. No. 4,873, 191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (*Lo, Mol. Cell. Biol.* 3:1803, 1983).

The present invention provides for transgenic animals that carry an oct-3 transgene in all of their cells, as well as animals that carry a transgene in some, but not all of their cells. For example, the invention provides for mosaic animals. The oct-3 transgene can be integrated as a single transgene or in concatamers, for example, head-to-head tandems or head-to-tail tandems. The transgene can also be selectively introduced into, and activated in, a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that an oct-3 transgene be integrated into the chromosomal site of an endogenous oct-3 gene, gene targeting is preferred. Briefly, when such a technique is to be used, vectors containing some nucleotide sequences homologous to an endogenous oct-3 gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous oct-3 gene in only that cell type (Gu et al., *Science* 265:103, 1984). The regulatory sequences required for such a cell-type specific inactivation will depend upon the particular cell type of interest, and will be apparent to those of skill in the art. These techniques are useful for preparing "knock outs" having no functional oct-3 gene.

Once transgenic animals have been generated, the expression of the recombinant oct-3 gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of oct-3 gene-expressing tissue can also be evaluated immunocytochemically using antibodies specific for the OCT-3 transgene product.

For a review of techniques that can be used to generate and assess transgenic animals, those of ordinary skill in the art can consult Gordon (*Intl. Rev. Cytol.* 115:171–229, 1989), and may obtain additional guidance from, for example: Hogan et al. "Manipulating the Mouse Embryo" (Cold Spring Harbor Press, Cold Spring Harbor, N.Y., 1986; Krimpenfort et al., *Bio/Technology* 9:86, 1991; Palmiter et al., *Cell* 41:343, 1985; Kraemer et al., "Genetic Manipulation of the Early Mammalian Embryo," Cold Spring Harbor Press, Cold Spring Harbor, N.Y., 1985; Hammer et al., *Nature* 315:680, 1985; Purcel et al., *Science* 244:1281, 1986; Wagner et al., U.S. Pat. No. 5,175,385; and Krimpenfort et al., U.S. Pat. No. 5,175,384.

The transgenic animals of the invention can be used to determine the consequence of altering the expression of oct-3 in the context of various disease states. For example, oct-3 knock out mice can be generated using an established line of mice that serve as a model for a neurodegenerative disease. For example, oct-3 can be knocked out in mice bearing a mutation in the weaver gene, which allows them to serve as a model for Parkinson's Disease. If the symptoms (e.g., altered balance or gait) normally apparent in weaver mice are lessened when an oct-3 gene is no longer expressed, patients suffering from Parkinson's Disease are likely to benefit from treatment with any compound that decreases the expression of oct-3 or the activity of OCT-3.

IV. Anti-OCT-3 Antibodies

OCT-3 polypeptides (or immunogenic fragments or analogs thereof) can be used to raise antibodies useful in the invention; such polypeptides can be produced by recombinant techniques or synthesized (see, for example, "Solid Phase Peptide Synthesis," supra; Ausubel et al., supra). In general, OCT-3 polypeptides can be coupled to a carrier protein, such as KLH, as described in Ausubel et al., supra, mixed with an adjuvant, and injected into a host mammal. Antibodies produced in that animal can then be purified by peptide antigen affinity chromatography.

In particular, various host animals can be immunized by injection with a OCT-3 polypeptide or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and *Corynebacterium parvum*. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the OCT-3 polypeptides described above and standard hybridoma technology (see, for example, Kohler et al., *Nature* 256:495, 1975; Kohler et al., *Eur. J. Immunol.* 6:511, 1976; Kohler et al., *Eur. J. Immunol.* 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific OCT-3 recognition by Western blot or immunoprecipitation analysis by standard methods, for example, as described in Ausubel et al., supra. Antibodies that specifically recognize and bind to OCT-3 are useful in the invention. For example, such antibodies can be used in an immunoassay to monitor the level of OCT-3 produced by a mammal (e.g., to determine the amount or subcellular location of OCT-3).

There are two major classes of antibodies which are within the scope of the present invention. The first class are antibodies that selectively bind to OCT-3 polypeptide, not bind to other members of the OCT family of proteins. The second class are antibodies that bind to more than one member of the OCT family of proteins.

Preferably, OCT-3 selective antibodies of the invention are produced using fragments of the OCT-3 polypeptide that lie outside highly conserved regions (such as the TM domains and the regions shown in FIGS. 4A–4E) and appear likely to be antigenic, by criteria such as high frequency of charged residues. Cross-reactive anti-OCT-3 antibodies are produced using a fragment of OCT-3 that is conserved amoungst members of this family of proteins. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antiserum is also checked for its ability to immunoprecipitate recombinant OCT-3 polypeptides or control proteins, such as glucocorticoid receptor, CAT, or luciferase.

The antibodies can be used, for example, in the detection of OCT-3 in a biological sample as part of a diagnostic assay or to reduce OCT-3 activity as part of a theraputic regime (e.g., to reduce an undesirably high level of OCT-3 activity). Antibodies also can be used in a screening assay to measure the effect of a candidate compound on expression or localization of OCT-3. Additionally, such antibodies can be used in conjunction with the gene therapy techniques. For example, they may be used to evaluate the normal and/or engineered OCT-3-expressing cells prior to their introduction into the patient.

In addition, techniques developed for the production of "chimeric antibodies" (Morrison et al., *Proc. Natl. Acad. Sci.*

USA 81:6851, 1984; Neuberger et al., *Nature* 312:604, 1984; Takeda et al., *Nature* 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946,778, and 4,704,692) can be adapted to produce single chain antibodies against an OCT-3 polypeptide, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., *Science* 246:1275, 1989) to allow rapid and easy identification of monoclonal Fab fragments with the desired specificity.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., *Nature Genetics* 7:13–21, 1994; see also U.S. Pat. Nos. 5,545,806 and 5,569,825).

The methods described herein, in which anti-OCT-3 antibodies are employed, can be performed, for example, by utilizing pre-packaged diagnostic kits comprising at least one specific oct-3 nucleotide sequence or antibody reagent described herein, which may be conveniently used, for example, in clinical settings, to diagnose patients exhibiting symptoms of the disorders described below.

V. Antisense Nucleic Acid Molecules

Treatment regimes based on an "antisense" approach involve the design of oligonucleotides (either DNA or RNA) that are complementary to a portion of a selected mRNA. These oligonucleotides bind to complementary mRNA transcripts and prevent their translation. Absolute complementarity, although preferred, is not required. A sequence "complementary" to a portion of an RNA molecule, as referred to herein, is a sequence having sufficient complementarily to hybridize with the RNA, forming a stable duplex; in the case of double-stranded antisense nucleic acids, a single strand of the duplex DNA can be tested, or triplex formation can be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One of ordinary skill in the art can ascertain a tolerable degree of mismatch by use of standard procedures to determine the melting point of the hybridized complex.

Oligonucleotides that are complementary to the 5' end of the message, for example, the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, *Nature* 372:333, 1984). Thus, oligonucleotides complementary to either the 5' or 3' non-translated, non-coding regions of an oct-3 gene, for example, a human gene as shown in FIG. 1 or FIG. 2, could be used in an antisense approach to inhibit translation of endogenous oct-3 mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5', 3', or coding region of oct-3 mRNA, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

Regardless of the choice of target sequence, as with other therapeutic strategies directed to OCT-3, it is preferred that in vitro studies are first performed to assess the ability of an antisense oligonucleotide to inhibit gene expression. If desired, the assessment can be quantitative. It is preferred that these studies utilize controls that distinguish between antisense gene inhibition and any nonspecific biological effect that an oligonucleotide may incur. It is also preferred that these studies compare levels of the target RNA or protein with that of an internal control RNA or protein. Additionally, it is envisioned that results obtained using an antisense oligonucleotide are compared with those obtained using a control oligonucleotide. Preferably, the control oligonucleotide is of approximately the same length as the test oligonucleotide, and the nucleotide sequence of the control oligonucleotide differs from that of the test antisense sequence no more than is necessary to prevent specific hybridization between the control oligonucleotide and the targeted RNA sequence.

The oligonucleotides can contain DNA or RNA, or they can contain chimeric mixtures, derivatives, or modified versions thereof that are either single-stranded or double-stranded. The oligonucleotide can be modified at the base moiety, sugar moiety, or phosphate backbone, for example, to improve stability of the molecule, hybridization, etc. Modified sugar moieties can be selected from the group including, but not limited to, arabinose, 2-fluoroarabinose, xylulose, and hexose. A modified phosphate backbone can be selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

The oligonucleotide can include other appended groups such as peptides (e.g., for disrupting the transport properties of the molecule in host cells in vivo), or agents that facilitate transport across the cell membrane (as described, for example, in Letsinger et al., *Proc. Natl. Acad. Sci. USA* 86:6553, 1989; Lemaitre et al., *Proc. Natl. Acad. Sci. USA* 84:648, 1987; PCT Publication No. WO 88/09810) or the blood-brain barrier (see, for example, PCT Publication No. WO 89/10134), or hybridization-triggered cleavage agents (see, for example, Krol et al., *BioTechniques* 6:958, 1988), or intercalating agents (see, for example, Zon, *Pharm. Res.* 5:539, 1988). To this end, the oligonucleotide can be conjugated to another molecule, for example, a peptide, a hybridization triggered cross-linking agent, a transport agent, or a hybridization-triggered cleavage agent.

An antisense oligonucleotide of the invention can comprise at least one modified base moiety that is selected from the group including, but not limited to, 5-fluoro-uracil, 5-bromouracil, 5-chlorouracil, 5-iodouracil, hypoxanthine, xantine, 4-acetylcytosine, 5-(carboxyhydroxyl-methyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids. Res.* 15:6625, 1987). The oligonucleotide is a 2'-0-methylribonucleotide (Inoue et al., *Nucl. Acids Res.* 15:6131, 1987), or a chimeric RNA-DNA analog (Inoue et al., *FEBS Lett.* 215:327, 1987).

Antisense oligonucleotides of the invention can be synthesized by standard methods known in the art, for example, by use of an automated DNA synthesizer (such as are commercially available from Biosearch, Applied Biosystems, etc.). As examples, phosphorothioate oligonucleotides can be synthesized by the method of Stein et al. (*Nucl. Acids Res.* 16:3209, 1988), and methylphosphonate oligonucleotides can be prepared by use of controlled pore glass polymer supports (Sarin et al., *Proc. Natl. Acad. Sci. USA* 85:7448, 1988).

While antisense oligonucleotides that are complementary to the coding region of oct-3 could be used, those complementary to the transcribed untranslated region are most preferred.

For therapeutic application, antisense molecules of the invention should be delivered to cells that express oct-3 in vivo. A number of methods have been developed for delivering antisense DNA or RNA to cells; for example, antisense molecules can be injected directly into the tissue site. Alternatively, modified antisense molecules, which are designed to target cells that express oct-3 (e.g., antisense molecules linked to peptides or antibodies that specifically bind receptors or antigens expressed on the target cell surface) can be administered systemically.

However, it is often difficult to achieve intracellular concentrations of antisense molecules that are sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with endogenous oct-3 transcripts and thereby prevent translation of oct-3 mRNA. For example, a vector can be introduced in vivo in such a way that it is taken up by a cell and thereafter directs the transcription of an antisense RNA. Such a vector can remain episomal or become chromosomally integrated, as long as it can be transcribed to produce the desired antisense RNA.

Vectors encoding an oct-3 antisense sequence can be constructed by recombinant DNA technology methods that are standard practice in the art. Suitable vectors include plasmid vectors, viral vectors, or other types of vectors known or newly discovered in the art. The criterion for use is only that the vector be capable of replicating and expressing the oct-3 antisense molecule in mammalian cells. Expression of the sequence encoding the antisense RNA can be directed by any promoter known in the art to act in mammalian, and preferably in human, cells. Such promoters can be inducible or constitutively active and include, but are not limited to: the SV40 early promoter region (Bernoist et al., *Nature* 290:304, 1981); the promoter contained in the 3' long terminal repeat of Rous sarcoma virus (Yamamoto et al., *Cell* 22:787–797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

VI. Ribozymes

Ribozyme molecules designed to catalytically cleave oct-3 mRNA transcripts also can be used to prevent translation of oct-3 mRNA and expression of OCT-3 polypeptides (see, for example, PCT Publication WO 90/11364; Saraver et al., *Science* 247:1222, 1990). While various ribozymes that cleave mRNA at site-specific recognition sequences can be used to destroy oct-3 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature* 334:585, 1988). There are numerous examples of potential hammerhead ribozyme cleavage sites within the nucleotide sequence of human oct-3 cDNA. Preferably, the ribozyme is engineered so that the cleavage recognition site is located near the 5' end of the oct-3 mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in Tetrahymena Thermophila (known as the IVS or L-19 IVS RNA), and which has been extensively described by Cech and his collaborators (Zaug et al., *Science* 224:574, 1984; Zaug et al., Science 231:470, 1986; Zug et al., *Nature* 324:429, 1986; PCT Application No. WO 88/04300; and Been et al., *Cell* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in oct-3.

As in the antisense approach, the ribozymes can be composed of modified oligonucleotides (e.g., for improved stability, targeting, etc.), and should be delivered to cells which express the oct-3 in vivo. A preferred method of delivery involves using a DNA construct "encoding" the ribozyme under the control of a strong constitutive pol III or pol II promoter, so that transfected cells will produce sufficient quantities of the ribozyme to destroy endogenous oct-3 messages and inhibit translation. Because ribozymes, unlike antisense molecules, are catalytic, a lower intracellular concentration is required for efficiency.

VII. Peptide Nucleic Acids

Oct-3 nucleic acid molecules can be modified at the base moiety, sugar moiety, or phosphate backbone to improve, for example, the stability or solubility of the molecule or its ability to hybridize with other nucleic acid molecules. For example, the deoxyribose phosphate backbone of the nucleic acid can be modified to generate peptide nucleic acids (see Hyrup et al., *Bioorganic Med. Chem.* 4:5–23 (1996). As used herein, the terms "peptide nucleic acids" or "PNAs" refer to nucleic acid mimics, for example, DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., supra; Perry-O'Keefe et al. *Proc. Natl. Acad. Sci. USA* 93:14670–14675 (1996).

PNAs of oct-3 can be used in therapeutic and diagnostic applications. For example, PNAs can be used as antisense or antigene agents for sequence-specific modulation of gene expression by, for example, inducing transcription or translation arrest or inhibiting replication. PNAs of oct-3 can also be used, for example, in the analysis of single base pair mutations in a gene by, for example, PNA-directed PCR clamping; as artificial restriction enzymes when used in combination with other enzymes, for example, S1 nucleases (Hyrup et al., supra); or as probes or primers for DNA sequence and hybridization (Hyrup et al., supra; Perry-O'Keefe, supra).

In other embodiments, PNAs of oct-3 can be modified, for example, to enhance their stability or cellular uptake, by attaching lipophilic or other helper groups to the PNA, by the formation of PNA-DNA chimeras, or by the use of liposomes or other techniques of drug delivery known in the art. For example, PNA-DNA chimeras of oct-3 can be generated that may combine the advantageous properties of PNA and DNA. Such chimeras allow DNA recognition enzymes, for example, RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, supra). The synthesis of PNA-DNA chimeras can be performed as described in Hyrup, supra, and Finn et al., *Nucl. Acids Res.* 24:3357–3363 (1996). For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used between the PNA and the 5' end of DNA (Mag et al., *Nucl. Acids Res.* 17:5973–5988, 1989). PNA monomers are then coupled in a stepwise manner to produce a chimeric molecule with a 5' PNA segment and a 3' DNA segment (Finn et al., supra). Alternatively, chimeric molecules can be synthesized with a 5' DNA segment and a 3' PNA segment (Peterser et al., *Bioorganic Med. Chem. Lett.* 5:1119–11124 (1975).

In other embodiments, the oligonucleotide may include other appended groups such as peptides (e.g., for targeting host cell receptors in vivo), or agents facilitating transport across the cell membrane (see, e.g., Letsinger et al., *Proc. Natl. Acad. Sci. USA* 86:6553–6556 (1989); Lemaitre et al., *Proc. Natl. Acad. Sci. USA* 84:648–652 (1987); PCT Publication No. WO 88/09810, published Dec. 15, 1988) or the blood-brain barrier (see, e.g., PCT Publication No. WO 89/10134, published Apr. 25, 1988). In addition, oligonucleotides can be modified with hybridization-triggered cleavage agents (see, e.g., Krol et al., *BioTech.* 6:958–976 (1988)) or integrating agents (see, e.g., Zon, *Pharm. Res.* 5:539–549 (1988)). To this end, the oligonucleotide may be conjugated to another molecule, for example, a peptide, hybridization triggered corss-linking agent, transport agent, hybridization-triggered cleavage agent etc.

VIII. Proteins that Associate with OCT-3

The invention also features methods for identifying polypeptides that can associate with OCT-3, as well as the isolated interactor, for example, proteins that alter the ability of OCT-3 to transport molecules across the plasma membranes of cells in which it is expressed. Any method that is suitable for detecting protein-protein interactions can be employed to detect polypeptides that associate with OCT-3, whether these polypeptides associate with the transmembrane, intracellular, or extracellular domains of OCT-3. Among the traditional methods that can be employed are co-immuno-precipitation, crosslinking, and co-purification through gradients or chromatographic columns of cell lysates or proteins obtained from cell lysates and the use of OCT-3 to identify proteins in the lysate that interact with OCT-3. For these assays, the OCT-3 polypetide can be a full length OCT-3, an extracellular domain of OCT-3, or some other suitable OCT-3 polypeptide. Once isolated, such an interacting protein can be identified and cloned and then used, in conjunction with standard techniques, to alter the activity of the OCT-3 polypeptide with which it interacts. For example, at least a portion of the amino acid sequence of a protein that interacts with OCT-3 can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel, supra; and "PCR Protocols: A Guide to Methods and Applications," Innis et al., eds. Academic Press, Inc., NY, 1990).

Additionally, methods can be employed that result directly in the identification of genes that encode proteins that interact with OCT-3. These methods include, for example, screening expression libraries, in a manner similar to the well known technique of antibody probing of λgt11 libraries, using labeled OCT-3 polypeptide or an OCT-3 fusion protein, for example, an OCT-3 polypeptide or domain fused to a marker such as an enzyme, fluorescent dye, a luminescent protein, or to an IgFc domain.

There are also methods available that can detect protein-protein interaction in vivo. A method which detects protein interactions in vivo is the two-hybrid system (Chien et al., *Proc. Natl. Acad. Sci. USA* 88:9578, 1991). A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding OCT-3, an OCT-3 polypeptide, or an OCT-3 fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or LacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, OCT-3 may be used as the bait gene product. Total genomic or cDNA sequences are fused to the DNA encoding an activation domain. This library and a plasmid encoding a hybrid of bait OCT-3 gene product fused to the DNA-binding domain are cotransformed into a yeast reporter strain, and the resulting transformants are screened for those that express the reporter gene. For example, a bait oct-3 gene sequence, such as oct-3 or a domain of oct-3 can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait oct-3 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait oct-3 gene-GAL4 fusion plasmid into a yeast strain which contains a lacZ gene driven by a promoter which contains GAL4 activation sequence. A cDNA encoded protein, fused to GAL4 transcriptional activation domain, that interacts with bait oct-3 gene product will reconstitute an active GAL4 protein and thereby drive expression of the HIS3 gene. Colonies that express HIS3 can then be purified from these strains and used to produce and isolate the bait oct-3 gene-interacting protein using techniques routinely practiced in the art.

IX. Detection of Oct-3 Protein or Nucleic Acid and Diagnostic Assays

The invention encompasses methods for detecting the presence of Oct-3 protein or nucleic acid in a biological sample as well as methods for measuring the level of Oct-3 protein or nucleic acid in a biological sample. Such methods are useful for diagnosis of disorders associated with aberrant expression of OCT-3.

An exemplary method for detecting the presence or absence of OCT-3 in a biological sample involves obtaining a biological sample from a test subject and contacting the biological sample with a compound or an agent capable of detecting an OCT-3 polypeptide or an oct-3 nucleic acid (e.g., mRNA or genomic DNA) that encodes an OCT-3 polypeptide. A preferred agent for detecting oct-3 mRNA or genomic DNA is a labeled nucleic acid probe capable of hybridizing to oct-3 mRNA or genomic DNA. The nucleic acid probe can be, for example, a full-length oct-3 nucleic acid molecule, such as a nucleic acid molecule having the sequence of SEQ ID NO:1, SEQ ID NO:3, or SEQ ID NO:5, or a portion thereof, such as an oligonucleotide of at least 15, 30, 50, 100, 250, or 500 nucleotides in length and sufficient to specifically hybridize under stringent conditions to oct-3 mRNA or genomic DNA.

A preferred agent for detecting an OCT-3 polypeptide is an antibody capable of binding to an OCT-3 polypeptide, preferably an antibody with a detectable label. Antibodies can be polyclonal, or more preferably, monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells and fluids present within a subject. That is, the detection method of the invention can be used to detect oct-3 mRNA, an OCT-3 polypeptide, or oct-3 genomic DNA in a biological sample in vitro as well as in vivo. For example, in vitro techniques for detection of oct-3 mRNA include Northern hybridizations and in situ hjybridizations. In vitro techniques for detection of an OCT-3 polypeptide include enzyme linked immunosorbent assays (ELISAs), Western blots, immunoprecipitations and immunofluorescence. In vitro techniques for detection of oct-3 genomic DNA include Southern hybridizations. Furthermore, in vivo techniques for detection of an OCT-3 polypeptide include introducing into a subject a labeled anti-OCT-3 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the subject.

In another embodiment, the methods further involve obtaining a control biological sample from a control subject, contacting the control sample with a compound or agent capable of detecting an OCT-3 polypeptide, oct-3 mRNA, or oct-3 genomic DNA, such that the presence of an OCT-3 polypeptide, oct-3 mRNA, or oct-3 genomic DNA is detected in the biological sample, and comparing the presence of OCT-3 polypeptide, oct-3 mRNA, or genomic DNA in the control sample with the presence of OCT-3 polypeptides, mRNA or genomic DNA in a test sample.

The invention also encompasses kits for detecting the presence of oct-3 nucleic acid molecules or OCT-3 polypeptides in a biological sample. For example, the kit can contain a labeled compound or agent capable of detecting an OCT-3 polypeptide or an oct-3 mRNA molecule in a biological sample; means for determining the amount of OCT-3 in the sample; and means for comparing the amount of OCT-3 in the sample with a standard. The compound or agent can be packaged in a suitable container. The kit can further contain instructions for using the kit to detect an OCT-3 polypeptide or oct-3 nucleic acid molecule.

X. Prognostic Assays

The invention also encompasses prognostic assays that can be used to identify subjects having or at risk of developing a disease or disorder associated with aberrant oct-3 expression or OCT-3 activity, e.g., a neurological disorder. Thus, the present invention provides a method for identifying a disease or disorder associated with aberrant oct-3 expression or OCT-3 activity in which a test sample is obtained from a subject and oct-3 nucleic acid molecules or OCT-3 polypeptides are detected, wherein the presence of oct-3 nucleic acid or OCT-3 polypeptides can be diagnostic for a subject having or at risk of developing an OCT-3 mediated disease or disorder based on the level of oct-3 expressed or the allelic form of OCT-3 expressed. As used herein, a "test sample" refers to a biological sample obtained from a subject of interest. For example, a test sample can be a biological fluid (e.g., serum), a cell sample, or tissue.

Furthermore, the prognostic assays described herein can be used to determine whether a subject can be administered an agent (e.g., an agonist, antagonist, peptidomimetic, polypeptide, nucleic acid, small molecule or other drug candidate) to treat a disease or disorder associated with aberrant oct-3 expression or OCT-3 activity. For example, such methods can be used to determine whether a subject can be effectively treated with an agent that modulates OCT-3 expression and/or activity. Thus, the present invention provides methods for determining whether a subject can be effectively treated with an agent for a disorder associated with aberrant oct-3 expression or OCT-3 activity in which a test sample is obtained and oct-3 nucleic acids or OCT-3 polypeptides are detected (e.g., wherein the presence of a particular level of oct-3 expression or a particular OCT-3 allelic variant is diagnostic for a subject that can be administered an agent to treat a disorder associated with aberrant oct-3 expression or OCT-3 activity).

The methods of the invention can also be used to detect genetic alterations in an oct-3 gene, thereby determining if a subject with the lesioned gene is at risk for a disorder characterized by aberrant extracellular concentrations of molecules normally transported across the cellular membrane by OCT-3. In preferred embodiments, the methods include detecting, in a sample of cells from the subject, the presence or absence of a genetic alteration characterized by at least one alteration affecting the integrity of the gene encoding an OCT-3 polypeptide or the misexpression of the oct-3 gene. For example, such genetic alterations can be detected by ascertaining the existence of at least one of: (1) a deletion of one or more nucleotides from an oct-3 gene; (2) an addition of one or more nucleotides to an oct-3 gene; (3) a substitution of one or more nucleotides of an oct-3 gene; (4) a chromosomal rearrangement of an oct-3 gene; (5) an alteration in the level of a messenger RNA transcript of an oct-3 gene; (6) aberrant modification of an oct-3 gene, such as of the methylation pattern of the genomic DNA, (7) the presence of a non-wild type splicing pattern of a messenger RNA transcript of an oct-3 gene; and (10) inappropriate post-translational modification of an OCT-3 polypeptide. As described herein, there are a large number of assay techniques known in the art which can be used for detecting alterations in an oct-3 gene. A preferred biological sample is a peripheral blood leukocyte sample isolated by conventional means from a subject.

In certain embodiments, detection of the alteration involves the use of a probe/primer in a polymerase chain reaction (PCR; see, e.g., U.S. Pat. Nos. 4,683,195 and 4,683,202), such as anchor PCR or RACE PCR, or alternatively, in a ligation chain reaction (LCR; see, e.g., Landegran et al., *Science* 241:1077–1080, 1988); and Nakazawa et al. *Proc. Natl. Acad. Sci. USA* 91:360–364, 1994), the latter of which can be particularly useful for detecting point mutations in the oct-3 gene (see Abavaya et al., *Nucl. Acids Res.* 23:675–681, 1995). This method can include the steps of collecting a sample of cells from a patient, isolating nucleic acid (e.g., genomic DNA, mRNA, or both) from the cells of the sample, contacting the nucleic acid sample with one or more primers which specifically hybridize to an oct-3 gene under conditions such that hybridization and amplification of the oct-3 nucleic acid (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., *Proc. Natl. Acad. Sci USA* 87:1874–1878, 1990), transcriptional amplification system (Kwoh et al., *Proc. Natl. Acad. Sci USA* 86:1173–1177, 1989), Q-Beta Replicase (Lizardi et al., *Bio/Technology* 6:1197, 1988), or any other nucleic acid amplification method, followed by the detection of the amplified molecules using techniques well known to those of ordinary skill in the art. These detection schemes are especially useful for the detection of nucleic acid molecules if such molecules are present in very low number.

In an alternative embodiment, alterations in an oct-3 gene from a sample cell can be identified by identifying changes in a restriction enzyme cleavage pattern. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, alterations in oct-3 can be identified by hybridizing a sample and control nucleic acids, e.g., DNA or RNA, to high density arrays containing tens to thousands of oligonucleotide probes (Cronin et al., *Human Mutation* 7:244–255 (1996); Kozal et al., *Nature Medicine* 2:753–759 (1996)). For example, alterations in oct-3 can be identified in two dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the oct-3 gene and detect mutations by comparing the sequence of the sample oct-3 with the corresponding wild-type (control) sequence. Examples of sequencing reactions include those based on techniques developed by Maxim and Gilbert (*Proc. Natl. Acad. Sci. USA* 74:560 (1977)) or Sanger (*Proc. Natl. Acad. Sci. USA* 74:5463). It is also contemplated that any of a variety of automated sequencing procedures can be utilized when performing the diagnostic assays (*Bio/Techniques* 19:448 (1995)) including sequencing by mass spectrometry (see, e.g. PCT International Publication No. WO 94/16101; Cohen et al. *Adv. Chromatogr.* 36:127–162 (1996); and Griffin et al. *Appl. Biochem. Biotechnol.* 38:147–159 (1993)).

Other methods of detecting mutations in the oct-3 gene include methods in which protection from cleavage agents is used to detect mismatched bases in RNA/RNA or RNA/DNA heteroduplexes (Myers et al. *Science* 230:1242 (1985)). In general, the art technique of "mismatch cleavage" starts by providing heteroduplexes formed by hybridizing (labeled) RNA or DNA containing the wild-type oct-3 sequence with potentially mutant RNA or DNA obtained from a tissue sample. The double-stranded duplexes are treated with an agent which cleaves single-stranded regions of the duplex such as which will exist due to basepair mismatches between the control and smaple strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al., *Proc. Natl. Acad. Sci. USA* 85:4397 (1988); Saleeba et al., *Methods Enzymol.* 217:286–295 (1992). In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in oct-3 cDNAs obtained from samples of cells. For example, the mutY enzyme of *E. coli* cleaves A at G/A mismatches (Hsu et al. *Carcinogenesis* 15:1657–1662 (1994)). According to an exemplary embodiment, a probe based on an oct-3 sequence is hybridized to a cDNA or other DNA product from a test cell or cells. The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility can be used to identify mutations in oct-3 genes. For example, single strand conformation polymorphism (SSCP) can be used to detect differences in electrophoretic mobility between mutant and wild type nucleic acids (Orita et al., *Proc. Natl. Acad. Sci. USA* 86:2766, see also Cotton *Mutat Res.* 285:125–144 (1993); and Hayashi *Genet. Anal. Tech. Appl.* 9:73–79 (1992)). Single-stranded DNA fragments of sample and control oct-3 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the method utilizes heteroduplex analysis to separate double stranded heteroduplex molecules on the basis of changes in electrophoretic mobility (Kee et al. *Trends Genet.* 7:5 (1991)).

In yet another embodiment, the movement of mutant or wild-type fragments in a polyacrylamide gel containing a gradient of denaturant is assayed using denaturing gradient gel electrophoresis (DGGE; Myers et al. *Nature* 313:495 (1985)). When DGGE is used as the method of analysis, DNA will be modified to insure that it does not completely denture, for example by adding a GC clamp of approximtely 40 bp of high-melting GC-rich DNA by PCR. In a further embodiment, a temperature gradient is used in place of a denaturing gradient to identify differences in the mobility of control and sample DNA (Rosenbaum et al. *Biophys. Chem.* 265:12753 (1987)).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. *Nature* 324;163 (1986); Saiki et al., *Proc. NAtl. Acad. Sci. USA* 86:6230 (1989)). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule, so that amplification depends on differential hybridization (Gibbs et al., *Nucl. Acids Res.* 17:2437–2448 (1989)) or at the extreme 3' end of one primer where, under appropriate conditions, mismatch can prevent, or reduce polymerase extension (Prossner, *Tib/Tech* 11:238 (1993)). In addition it may be desirable to introduce a novel restriction site in the region of the mutation to create cleavage-based detection (Gasparini et al., *Mol. Cell Probes* 6:1 (1992)). It is anticipated that in certain embodiments amplification may also be performed using Taq ligase for amplification (Barany, *Proc. Natl. Acad. Sci. USA* 88:89 (1991)). In such cases, ligation will occur only if there is a perfect match at the 3' end of the 5' sequence making it possible to detect the presence of a known mutation at a specific site by looking for the presence of absence of amplification.

The methods described herein may be performed, for example, by utilizing pre-packaged diagnostic kits comprising at least one probe nucleic acid or antibody reagent described herein, which may be conveniently used, for example, in a clinical setting to diagnose patient exhibiting symptoms or a family history of a disease or disorder involving abnormal OCT-3 activity.

XI. Pharmacogenetics

Agents or modulators which have a stimulatory or inhibitory effect on OCT-3 activity (including those that alter activity by altering oct-3 gene expression), identified by a screening assay described herein, can be administered to individuals to treat, prophylactically or therapeutically, disorders (e.g., neurological disorders) associated with aberrant OCT-3 activity. In conjunction with such treatment, the pharmacogenetics (i.e., the study of the relationship between an individual's genotype and that individual's response to a foreign compound or drug) of the individual may be considered. Thus, the pharmacogenetics of the individual permits the selection of effective agents (e.g., drugs) for prophylactic or therapeutic treatments based on a consideration of the individual's genotype. Such pharmacogenetics can further be used to determine appropriate dosages and therapeutic regimens. Accordingly, the activity of OCT-3 polypeptides, expression of oct-3 nucleic acids, or mutation content of oct-3 genes in an individual can be determined to thereby select appropriate agents for therapeutic or prophylactic treatment of the individual.

Pharmacogenetics deals with clinically significant hereditary variations in the response to drugs due to altered drug disposition and abnormal action in affected persons. See, e.g., Eichelbaum, *Clin. Exp. Pharmacol. Physiol.* 23:983–985 (1996) and Linder, *Clin. Chem.* 43:254–266 (1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinicl complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g. N-acetyltransferase (NAT2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensize metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme is the so called ultr-rapid metabolizers who do not respond to standard doses. Recently, the molecular basis of ultr-rapid metabolism has been identified to be due to CYP2D6 gene amplification.

Thus, the activity of OCT-3 polypeptide, expression of oct-3 nucleic acid, or mutation content of oct-3 gene in an individual can be determined to thereby select appropriate agents for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an OCT-3 modulator, such as a modulator identified by one of the exemplary screening assays described herein.

XII. Monitoring of Effects During Clinical Trials

Monitoring the influence of agents (e.g., drugs, compounds) on the expression of oct-3 or the activity OCT-3 (e.g., the ability to modulate the symptoms associated with neurological disorders) can be applied not only in basic drug screening, but also in clinical trials. For example, the effectiveness of an agent determined by a screening assay as described herein to increase oct-3 gene expression, OCT-3 polypeptide levels, or upregulate OCT-3 activity, can be monitored in clinical trials of subjects exhibiting decreased oct-3 gene expression, decreased OCT-3 polypeptide levels, or downregulated OCT-3 activity. Alternatively, the effectiveness of an agent determined by a screening assay to decrease oct-3 gene expression, decrease OCT-3 polypeptide levels, or downregulate OCT-3 activity, can be monitored in clinical trials of subjects exhibiting increased oct-3 gene expression, increased OCT-3 polypeptide levels, or upregulated OCT-3 activity. In such clinical trials, the expression of oct-3 or activity of OCT-3 can be used as a "read out" or marker of the responsiveness of a particular cell.

For example, and not by way of limitation, genes, including oct-3, that are modulated in cells by treatment with an agent (e.g., a compound, drug, or small molecule) that modulates OCT-3 activity (e.g., identified in a screening assay as described herein) can be identified. Thus, to study the effect of agents on neurolgoical disorders, for example, in a clinical trial, cells can be isolated and RNA prepared and analyzed for the level of oct-3 expression and other genes implicated in the neurological disorder. The levels of gene expression (i.e., a gene expression pattern) can be quantified by Northern blot analysis or RT-PCR, as described herein, or alternatively by measuring the amount of polypeptide produced, by one of the methods described herein, or by measuring the levels of activity of OCT-3 or other genes. In this way, the gene expression pattern can serve as an indicative marker of the physiological response of the cells to the agent. Accordingly, this response state can be determined before, and at various points during, treatment of the individual with the agent.

In a preferred embodiment, the present invention provides a method for monitoring the effectiveness of treatment of a subject with an agent (e.g., an agonist, antagonist, peptidomimetic, polypeptide, nucleic acid, small molecule, or other drug candidate identified by the ascreening assays described herein) comprising the steps of (1) obtaining a pre-administration sample from a subject prior to administration of the agent; (2) detecting the level of expression of an OCT-3 polypeptide or oct-3 mRNA in the pre-administration sample, or the level or activity of oct-3; (3) obtaining one or more post-administration samples from the subject; (4) detecting the level of expression of oct-3 mRNA or the level or activity of the OCT-3 polypeptide in the post-administration sample; (5) comparing the level of expression of oct-3 mRNA in the pre-administration sample with that in the post-administration sample, or comparing the level or activity of the OCT-3 polypeptide in the pre-administration sample with that in the post-administration sample; and (6) altering the administration of the agent to the subject accordingly.

XIII. Screening Assays for Compounds that Modulate OCT-3 Expression or Activity

The invention also encompasses methods for identifying compounds that interact with OCT-3 (or a domain of OCT-3) including, but not limited to, compounds that interfere with the interaction of OCT-3 with transmembrane or intracellular proteins which regulate OCT-3 activity and compounds which modulate OCT-3 activity. Also encompasses are method for identifying compounds which bind to Oct-3 gene regulatory sequences (e.g., promoter sequences) and which may modulate Oct-3 gene expression.

The compounds which may be screened in accordance with the invention include, but are not limited to peptides, antibodies and fragments thereof, and other organic compounds that bind to OCT-3 and increase or decrease activity.

Such compounds may include, but are not limited to, peptides such as, for example, soluble peptides, including but not limited to members of random peptide libraries; (Lam et al., *Nature* 354:82–84, 1991; Houghten et al., *Nature* 354:84–86, 1991), and combinatorial chemistry-derived molecular library made of D- and/or L- configuration amino acids, phosphopeptides (including, but not limited to, members of random or partially degenerate, directed phosphopeptide libraries; Songyang, et al., *Cell* 72:767–778, 1993), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds which can be screened in accordance with the invention include but are not limited to small organic molecules that are able to gain entry into an appropriate cell and affect the expression of the Oct-3 gene or activity of Oct-3 protein.

Computer modelling and searching technologies permit identification of compounds, or the improvement of already identified compounds, that can modulate OCT-3 expression or activity. Having identified such a compound or composition, the active sites or regions are identified. Such active sites might typically be a binding for a natural modulator of activity. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the modulator (or ligand) is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed modulator (ligand), natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a seach can be manual, but is preferably computer assisted. These compounds found from this search are potential OCT-3 modulating compounds.

Alternatively, these methods can be used to identify improved modulating compounds from a previously identified modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Examples of molecular modelling systems are the CHARMm and QUANTA programs (Polygen Corporation, Waltham, MA). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen et al. Acta Pharmaceutical Fennica 97:159–166, 1993; Ripka, New Scientist 54–57 (Jun. 16, 1988); McKinaly and Rossmann, Annu. Rev. Pharmacol. Toxiciol. 29:111–122, 1989; Perry and Davies, OSAR: Quantitative Structure-Activity Relationships in Drug Design, pp. 189–193 (Alan R. Liss, Inc. 1989); Lewis and Dean, 1989 Proc. R. Soc. Lond. 236:125–140 and 141–162; and, with respect to a model receptor for nucleic acid components, Askew et al., J. Am. Chem. Soc. 111:1082–1090, 1989. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators of OCT-3 activity (ion transport).

Compounds identified via assays such as those described herein may be useful, for example, in elaborating the biological function of OCT-3 and for the treatment of disorders associated with aberrant OCT-3 activity or expression. Assays for testing the effectiveness of compounds identified with the above-described techniques are are discussed below.

In vitro systems may be designed to identify compounds capable of interacting with OCT-3 (or a domain of OCT-3). Compounds identified may be useful, for example, in modulating the activity of wild type and/or mutant OCT-3; may be useful in elaborating the biological function of the OCT-3; may be utilized in screens for identifying compounds that disrupt normal OCT-3 interactions; or may in themselves disrupt such interactions.

The principle of the assays used to identify compounds that bind to the OCT-3 involves preparing a reaction mixture of OCT-3 (or a doamin thereof) and the test compound under conditions and for a time sufficient to allow the two components to interact and bind, thus forming a complex which can be removed and/or detected in the reaction mixture. The OCT-3 species used can vary depending upon the goal of the screening assay. In some situations it is preferable to employ a peptide corresponding to a domain of OCT-3 fused to a heterologous protein or polypeptide that affords advantages in the assay system (e.g., labeling, isolation of the resulting complex, etc.) can be utilized.

The screening assays can be conducted in a variety of ways. For example, one method to conduct such an assay involves anchoring the OCT-3 protein, polypeptide, peptide or fusion protein or the test substance onto a solid phase and detecting OCT-3/test compound complexes anchored on the solid phase at the end of the reaction. In one embodiment of such a method, the OCT-3 reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for OCT-3 protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with OCT-3. To this end, cell lines that express OCT-3, or cell lines that have been genetically engineered to express OCT-3 can be used.

XIV. Assays for Compounds that Interfere with Proteins that Interact with OCT-3

Proteins that interact with the OCT-3 are referred to, for purposes of this discussion, as "binding partners". Such binding partners are involved in regulating OCT-3 activity. Therefore, it is desirable to identify compounds that interfere with or disrupt the interaction of such binding partners with OCT-3. Such compounds may be useful in regulating the activity of the OCT-3 and treating disorders associated with aberrant OCT-3 activity.

The basic principle of the assay systems used to identify compounds that interfere with the interaction between the OCT-3 and its binding partner or partners involves preparing a reaction mixture containing OCT-3 protein, polypeptide, peptide or fusion protein and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the OCT-3 moiety and its binding partner. Control reaction mixtures are incubated without the test compound or with a non-active control compound. The formation of any complexes between the OCT-3 moiety and the binding partner is then detected. The formation of a complex in the control reaction, but not in the reaction mixture containing the test compound, indicates that the compound interferes with the interaction of the OCT-3 and the interactive binding partner. Additionally, complex formation within reaction mixtures containing the test compound and normal OCT-3 protein may also be compared to complex formation within reaction mixtures containing the test compound and a mutant OCT-3. This comparison may be important in those cases wherein it is desirable to identify compounds that disrupt interactions of mutant but not normal OCT-3.

The assay for compounds that interfere with the interaction of the OCT-3 and binding partners can be conducted in a heterogeneous or homogeneous format. Heterogeneous assays involve anchoring either the OCT-3 protein, polypeptide, peptide, or fusion protein, or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the OCT-3 moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the OCT-3 moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of OCT-3 (or a doamin thereof) or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface, e.g., using a directly or indirectly labeled antibody specific for the initially non-immobilized species. Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected, e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the OCT-3 moiety and the interactive binding partner is prepared in which either the OCT-3 or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt OCT-3/intracellular binding partner interaction can be identified.

In a particular embodiment, an OCT-3 fusion can be prepared for immobilization. For example, the OCT-3 or a peptide fragment thereof can be fused to a glutathione-S-transferase (GST) gene using a fusion vector, such as pGEX-5x-1, in such a manner that its binding activity is maintained in the resulting fusion protein. The interactive binding partner can be purified and used to raise a monoclonal antibody, using methods routinely practiced in the art. This antibody can be labeled with the radioactive isotope $^{125}$I, for example, by methods routinely practiced in the art. In a heterogeneous assay, the GST-OCT-3 fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between OCT-3 and the interactive binding partner can be detected by measuring the amount of radioactivity that remains associated with the glutathione-agarose beads. A successful inhibition of the interaction by the test compound will result in a decrease in measured radioactivity.

Alternatively, the GST-OCT-3 fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the OCT-3/binding partner interaction can be detected by adding the labeled antibody and measuring the radioactivity associated with the beads.

In another embodiment of the invention, these same techniques can be employed using peptide fragments that correspond to the binding domains of the OCT-3 and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

XV. Methods for Reducing Oct-3 Expression

Oct-3 expression can be reduced through the use of modulatory compounds identified through the use of the screening methods described above. In addition, endogenous oct-3 gene expression can also be reduced by inactivating or "knocking out" the oct-3 gene or its promoter using targeted homologous recombination (see, for example, U.S. Pat. No. 5,464,764). For example, a mutant, non-functional oct-3 (or a completely unrelated DNA sequence) flanked by DNA homologous to the endogenous oct-3 gene (either the coding regions or regulatory regions of the oct-3 gene) can be used, with or without a selectable marker and/or a negative selectable marker, to transfect cells that express oct-3 in vivo. Insertion of the DNA construct, via targeted homologous recombination, results in inactivation of the oct-3 gene. Such approaches are particularly suited for use in developing animal models to study the role of OCT-3; in this instance, modifications to ES (embryonic stem) cells can be used to generate animal offspring with an inactive oct-3 gene. However, a knock out approach can be adapted for use in humans, provided the recombinant DNA constructs are directly administered or targeted to the required site in vivo using appropriate viral vectors.

Alternatively, endogenous oct-3 gene expression can be reduced by targeting deoxyribonucleotide sequences complementary to the regulatory region of the oct-3 gene (i.e., the oct-3 promoter and/or enhancers) to form triple helical structures that prevent transcription of the oct-3 gene in target cells in the body (Helene, Anticancer Drug Res. 6:569, 1981; Helene et al., Ann. N.Y. Acad. Sci. 660:27, 1992; and Maher, *Bioassays* 14:807, 1992).

In addition, as discussed above, anti-sense moleceules, ribozymes, and peptide nucleic acids can be used to reduce oct-3 expression.

XVI. Assays for the Identification of Compounds that Ameliorate Disorders Associated with Aberrant OCT-3 Expression or Activity Compounds, including, but not limited to, compounds identified via assay techniques such as those described above may be useful for the treatment of disorders associated with aberrant OCT-3 activity.

While animal model-based assays are particularly useful for the identification of such therapeutic compounds, cell-based assay systems are also very useful, particularly in combination with animal-model based assays. Such cell-based systems can include, for example, recombinant or non-recombinant cells which express OCT-3. The effect of a selected modulatory compound on OCT-3 expression can be measured using any of the above-described techniques for measuring OCT-3 protein or Oct-3 mRNA, and the effect of a selected modulatory compound on OCT-3 activity can be measured by measuring the flux of a molecule transported by OCT-3.

XVII. Effective Dose

Toxicity and therapeutic efficacy of the polypeptides of the invention and the compounds that modulate their expression or activity can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

XVIII. Formulations and Use

Pharmaceutical compositions for use in accordance with the present invention can be formulated in a conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Alternatively, the active ingredient can be in powder form for constitution with a suitable vehicle, for example, sterile pyrogen-free water, before use.

The compounds can also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (e.g., subcutaneously or intramuscularly) or by intramuscular injection. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The compositions can, if desired, be presented in a pack or dispenser device which may contain one or more unit dosage forms containing the active ingredient. The pack can, for example, comprise metal or plastic foil, such as a blister pack. The pack or dispenser device can be accompanied by instructions for administration.

The therapeutic compositions of the invention can also contain a carrier or excipient, many of which are known to persons of ordinary skill in the art. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol.

The nucleic acids, polypeptides, antibodies, or other modulatory compounds of the invention (i.e., compounds that alter the expression of oct-3 or the activity of OCT-3) can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that the preferred route of administration will be intravenous.

XIX. Compounds Transported by OCT-3

Compounds that are transported across cellular membranes by an OCT-3 polypeptide of the invention can be identified by transiently expressing an oct-3 gene of the invention in cells (e.g., 293 cells) and measuring the transport of candidate molecules across the plasma membranes of those cells. The expression of an OCT-3 polypeptide could be confirmed by, for example, performing immunohistochemistry to detect either OCT-3 or an epitope tag placed on the OCT-3 polypeptide. To measure the transport of candidate molecules across the plasma membrane, one could directly measure the uptake of radiolabelled molecules such as TEA, dopamine, serotonin, histamine, and acetylcholine. This assay could be performed, for example, by incubating the cells expressing the OCT-3 transporter with radiolabelled candidate molecules for 1 hour at room temperature, washing the cells with an ice cold buffer, lysing the cells, and measuring the radioactivity in scintillant in a beta counter. Persons of ordinary skill in the art may consult Martel et al. (*Arch. Pharmacol.* 354:320–326, 1996), if necessary, for a more detailed protocol.

The assay described above can be used to determine whether any given polypeptide functions as an OCT-3 polypeptide of the invention. To make this determination, one would simply perform the assay using the OCT-3 polypeptide described herein and a second, putative OCT-3 polypeptide (such as a polypeptide that differs from SEQ ID NO:2 by the addition, deletion, or substitution of one or more amino acid residues), in parallel. The putative OCT-3 polypeptide would prove to be within the scope of the present invention if it exhibited 20%, 40%, or 50% of the activity of the full-length, mature form of OCT-3. Preferably, a candidate OCT-3 molecule would exhibit 75%, 80%, or even 90% (or more, e.g., 95% or even 99%) of the activity of OCT-3, as disclosed herein. Candidate OCT-3 polypeptides that are substantially identical to SEQ ID NO:2 may even exhibit greater biological activity (i.e., serve as more effective transporters) than the wild-type polypeptide itself.

XX. EXAMPLES

Examples 1 and 2 describe the identification and characterization of rat and human oct-3 nucleic acid molecules, respectively.

Example 1

A cDNA library in plasmid pMET7 was prepared using oligo dT-purified RNA isolated from adult rat frontal cortex tissue. The library was plated, colonies were selected randomly, and the 5' ends of the cDNA inserts were sequenced (5' sample sequencing). Each sequence (5' expressed sequence tag (EST)) was compared with sequences in public databases using the BLAST algorithm. One such 5' EST had an extremely low degree of similarity with OCT-2 sequences identified in pig and rat, and lesser similarity to nucleic acid molecules encoding other organic cation transport proteins. The sequence comparison indicated that the clone identified from the rat library was a partial length clone having a coding sequence that extended from approximately the 5' end of the sixth putative transmembrane domain through the 3' end of the gene. This clone was sequenced by sequentially "walking" from both the 5' and the 3' ends of the molecule. A hydropathy plot of the coding region indicated 7 transmembrane domains corresponding, approximately, in position to the sixth through the twelfth transmembrane domains of OCT-2. No stop codons were found in the homologous reading frame and a poly-A tail was detected. These features indicate that this is a legitimate, functional mRNA, rather than a pseudogene.

The 5' EST sequence was used to prepare a DNA probe that was labelled and hybridized to Northern blots. Hybridization to a blot containing several rat tissues (a rat multiple tissue Northern blot was purchased from Clontech) indicated a robust signal corresponding to a 2.3 kb transcript predominantly in brain tissues. Extended exposure of the autoradiogram prepared from the Northern blot indicated the presence of similar bands in a subset of other tissues including kidney, heart, lung, testis, spleen, and liver.

The rat RNA probe was also hybridized to a Northern blot containing samples from different regions of the human CNS, including spinal cord and cortex. A single band was observed in all samples. The intensity of labelling was similar in all samples, although somewhat reduced in the spinal cord.

The rat OCT-3 clone was used to make probes for in situ hybridization experiments. Experiments with various coronal sections of rat brain showed strong hybridization at the cell bodies of neurons. No significant hybridization was observed to non-neuronal cells. The hybridization signal at some neurons, for example, Purkinje cells, was relatively weak, while in other cells, for example, granule cells of the hippocampus and cerebellum, the hybridization signal was intense.

The sequence of the rat cDNA clone described in this example and the predicted amino acid sequence is shown in FIG. 3.

Example 2

The rat OCT-3 clone described in Example 1 was used to identify a portion of a human OCT-3 cDNA clone, which was used to screen a human cerebellum cDNA library. Seventy-seven clones were identified, and the 5' ends of 10 of these were sequenced and found to represent the same gene. Restriction digests of the plasmids showed two classes of insert lengths. One insert was approximately 1.5 kb and the other was approximately 2.4 kb. Two clones, designated "g" and "a," were selected as examples of each class and fully sequenced. Clone "a" has 12 hydrophobic transmembrane regions (as predicted by the Kyte and Doolittle algorithm), which is characteristic of transporter proteins. The sequence of clone "a" is shown in FIG. 1 (SEQ ID NO:1). Clone "g" represents a truncated mRNA whose coding region includes the first six TM domains. The sequence of clone "g" is shown in FIG. 2 (SEQ ID NO:3).

XXI. Deposit Statement

The subject clones have been deposited under conditions that assure that access to them will be available during the pendency of the patent application in which they are disclosed to those determined by the Commissioner of Patents and Trademarks to be entitled thereto under 37 C.F.R. 1.14 and 35 U.S.C. § 122. More specifically, the clones described herein as "g" and "a" were deposited with the American Type Culture Collection and assigned accession numbers 98518 and 98519, respectively.

What is claimed is:

1. An isolated nucleic acid molecule selected from the group consisting of:
   a) a nucleic acid molecule which encodes a polypeptide comprising the amino acid sequence of SEQ ID NO:2;
   b) a nucleic acid molecule which encodes a polypeptide comprising the amino acid sequence of SEQ ID NO:4; and
   c) a nucleic acid molecule which encodes a polypeptide comprising the amino acid sequence of SEQ ID NO:6.

2. An isolated nucleic acid molecule selected from the group consisting of:
   a) a nucleic acid molecule which encodes a polypeptide consisting of the amino acid sequence of SEQ ID NO:2;
   b) a nucleic acid molecule which encodes a polypeptide consisting of the amino acid sequence of SEQ ID NO:4; and
   c) a nucleic acid molecule which encodes a polypeptide consisting of the amino acid sequence of SEQ ID NO:6.

3. The isolated nucleic acid molecule of claim 1, wherein said nucleic acid molecule is selected from the group consisting of:
   a) a nucleic acid molecule comprising SEQ ID NO:1;
   b) a nucleic acid molecule comprising SEQ ID NO:3;
   c) a nucleic acid molecule comprising SEQ ID NO:5;
   d) a nucleic acid molecule consisting of SEQ ID NO:1;
   e) a nucleic acid molecule consisting of SEQ ID NO:3; and
   f) a nucleic acid molecule consisting of SEQ ID NO:5.

4. The isolated nucleic acid molecule of claim 2, wherein said nucleic acid molecule is selected from the group consisting of:
   a) a nucleic acid molecule comprising SEQ ID NO;1;
   b) a nucleic acid molecule comprising SEQ ID NO:3;
   c) a nucleic acid molecule comprising SEQ ID NO:5;
   d) a nucleic acid molecule consisting of SEQ ID NO:1;
   e) a nucleic acid molecule consisting of SEQ ID NO:3; and
   f) a nucleic acid molecule consisting of SEQ ID NO:5.

5. An isolated nucleic acid molecule which encodes a naturally-occurring OCT-3 polypeptide having at least 6 transmembrane domains, wherein said nucleic acid molecule hybridizes to a nucleic acid molecule consisting of the nucleotide sequence of SEQ ID NO:1 under conditions of hybridization at 42° C. in 2× SSC/0.1% SDS and of washing at 68° C. in 0.1× SSC.

6. An isolated nucleic acid molecule which encodes a naturally-occurring OCT-3 polypeptide having at least 6 transmembrane domains, wherein said nucleic acid molecule hybridizes to a nucleic acid molecule consisting of the nucleotide sequence of SEQ ID NO:3 under conditions of hybridization at 42° C. in 2× SSC/0.1% SDS and of washing at 68° C. in 0.1× SSC.

7. The nucleic acid molecule of claim 1 further comprising vector nucleic acid sequences.

8. The nucleic acid molecule of claim 2 further comprising vector nuclcic acid sequences.

9. The nucleic acid molecule of claim 3 further comprising vector nucleic acid sequences.

10. The nucleic acid molecule of claim 4 further comprising vector nucleic acid sequences.

11. The nucleic acid molecule of claim 1 wherein the polypeptide is a fusion polypeptide.

12. A host cell transformed to contain the nucleic acid molecule of claim 1.

13. A host cell transformed to contain the nucleic acid molecule of claim 2.

14. A host cell transformed to contain the nucleic acid molecule of claim 3.

15. A method for detecting the presence of a nucleic acid molecule that encodes a polypeptide consisting of the amino acid sequence of SEQ ID NO:2 in a sample, said method comprising the steps of:
   i) contacting a sample comprising nucleic acid molecules with a nucleic acid probe comprising the nucleic acid molecule of any one of claims 1, 2, 3, 4, 5, or 6;
   ii) determining whether the nucleic acid probe hybridizes to a nucleic acid molecule in said sample; and
   iii) determining that a nucleic acid molecule that encodes a polypeptide consisting of the amino acid sequence of SEQ ID NO:2 is present in said sample when said nucleic acid probe hybridizes to a nucleic acid molecule in said sample.

16. A method for detecting the presence of a nucleic acid molecule that encodes a polypeptide consisting of the amino acid sequence of SEQ ID NO:4 in a sample, said method comprising the steps of:
   i) contacting a sample comprising nucleic acid molecules with a nucleic acid probe comprising the nucleic acid molecule of any one of claims 1, 2, 3, 4, 5, or 6;
   ii) determining whether the nucleic acid probe hybridizes to a nucleic acid molecule in said sample; and
   iii) determining that a nucleic acid molecule that encodes a polypeptide consisting of the amino acid sequence of SEQ ID NO:4 is present in said sample when said nucleic acid probe hybridizes to a nucleic acid molecule in said sample.

17. An isolated nucleic acid molecule selected from the group consisting of:
   a) a nucleic acid molecule which encodes a polypeptide comprising the amino acid sequence encoded by the cDNA insert of the clone deposited with the ATCC® as Accession Number 98518; and
   b) a nucleic acid molecule which encodes a polypeptide comprising the amino acid sequence encoded by the cDNA insert of the clone deposited with the ATCC® as Accession Number 98519.

18. The isolated nucleic acid molecule of claim 1 which encodes a polypeptide comprising the amino acid sequence of SEQ ID NO:2.

19. The isolated nucleic acid molecule of claim 1 which encodes a polypeptide comprising the amino acid sequence of SEQ ID NO:4.

20. The isolated nucleic acid molecule of claim 1 which encodes a polypeptide comprising the amino acid sequence of SEQ ID NO:6.

21. The isolated nucleic acid molecule of claim 3 which comprises the nucleotide sequence of SEQ ID NO:1.

22. The isolated nucleic acid molecule of claim 3 which comprises the nucleotide sequence of SEQ ID NO:3.

23. The isolated nucleic acid molecule of claim 3 which comprises the nucleotide sequence of SEQ ID NO:5.

* * * * *